United States Patent
Kidwell, Jr. et al.

(10) Patent No.: US 10,618,079 B2
(45) Date of Patent: Apr. 14, 2020

(54) PIEZOELECTRIC MICROMECHANICAL ULTRASONIC TRANSDUCERS AND TRANSDUCER ARRAYS

(71) Applicant: QUALCOMM Incorporated, San Diego, CA (US)

(72) Inventors: Donald William Kidwell, Jr., Los Gatos, CA (US); Ravindra Vaman Shenoy, Dublin, CA (US); Jon Bradley Lasiter, Stockton, CA (US)

(73) Assignee: QUALCOMM Incorporated, San Diego, CA (US)

( * ) Notice: Subject to any disclaimer, the term of this patent is extended or adjusted under 35 U.S.C. 154(b) by 398 days.

(21) Appl. No.: 15/441,128

(22) Filed: Feb. 23, 2017

(65) Prior Publication Data

US 2017/0246662 A1 Aug. 31, 2017

Related U.S. Application Data

(60) Provisional application No. 62/301,532, filed on Feb. 29, 2016.

(51) Int. Cl.
*B06B 1/06* (2006.01)
*H01L 41/09* (2006.01)
(Continued)

(52) U.S. Cl.
CPC .......... *B06B 1/0622* (2013.01); *A61B 8/4494* (2013.01); *B06B 1/0603* (2013.01); *H01L 41/081* (2013.01)

(58) Field of Classification Search
CPC ... B06B 1/0622; B06B 1/0603; A61B 8/4494; H01L 41/081
(Continued)

(56) References Cited

U.S. PATENT DOCUMENTS

| 8,110,963 B2 | 2/2012 | Funasaka et al. |
| 8,406,084 B2 | 3/2013 | Buccafusca et al. |

(Continued)

FOREIGN PATENT DOCUMENTS

| CA | 2950919 A1 * | 1/2016 | ............ B06B 1/06 |
| CN | 104883979 A | 9/2015 | |

(Continued)

OTHER PUBLICATIONS

International Search Report and Written Opinion—PCT/US2017/019524—ISA/EPO—dated May 19, 2017.

*Primary Examiner* — Thomas M Dougherty
(74) *Attorney, Agent, or Firm* — Weaver Austin Villeneuve & Sampson LLP/QUALCOMM Incorporated

(57) ABSTRACT

An apparatus may include one or more segmented piezoelectric micromechanical ultrasonic transducer (PMUT) elements. Each segmented PMUT element may include a substrate, an anchor structure disposed on the substrate and a membrane disposed proximate the anchor structure. The membrane may include a piezoelectric layer stack and a mechanical layer. The anchor structure may include boundary portions that divide the segmented PMUT element into segments. Each segment may have a corresponding segment cavity. The boundary portions may correspond to nodal lines of the entire membrane. The membrane may include a membrane segment disposed proximate each segment cavity. The membrane may be configured to undergo one or both of flexural motion and vibration when the segmented PMUT element receives or transmits signals.

25 Claims, 18 Drawing Sheets

(51) Int. Cl.
*H01L 41/08* (2006.01)
*A61B 8/00* (2006.01)

(58) Field of Classification Search
USPC .................. 310/311, 322, 324, 328, 348
See application file for complete search history.

(56) References Cited

U.S. PATENT DOCUMENTS

| | | | |
|---|---|---|---|
| 9,331,666 | B2 | 5/2016 | Zuo et al. |
| 10,109,784 | B2 * | 10/2018 | Kidwell, Jr. ........... B06B 1/0622 |
| 2005/0169107 | A1 | 8/2005 | Thomenius et al. |
| 2014/0117812 | A1 | 5/2014 | Hajati |
| 2015/0265245 | A1 | 9/2015 | Von et al. |
| 2016/0107194 | A1 | 4/2016 | Panchawagh et al. |
| 2017/0021391 | A1 * | 1/2017 | Guedes ..................... B81B 3/00 |
| 2017/0320093 | A1 * | 11/2017 | Chatterjee ............. B06B 1/0622 |
| 2017/0328866 | A1 * | 11/2017 | Apte ....................... G01K 13/00 |

FOREIGN PATENT DOCUMENTS

| | | | | |
|---|---|---|---|---|
| CN | 105122488 | A | 12/2015 | |
| CN | 105247889 | A | 1/2016 | |
| JP | 2007229328 | A * | 9/2007 | |
| WO | WO2009088307 | A1 | 7/2009 | |
| WO | WO2012075106 | A1 | 6/2012 | |
| WO | WO2014065939 | A1 | 5/2014 | |
| WO | WO2016007250 | A1 | 1/2016 | |
| WO | WO-2016054447 | A1 * | 4/2016 | ............... B06B 3/00 |

* cited by examiner

PIEZOELECTRIC MICROMECHANICAL ULTRASONIC TRANSDUCERS AND TRANSDUCER ARRAYS

PRIORITY CLAIM

This application claims priority to U.S. Provisional Application No. 62/301,532, entitled "PIEZOELECTRIC MICROMECHANICAL ULTRASONIC TRANSDUCER HARMONIC ARRAYS" and filed on Feb. 29, 2016, which is hereby incorporated by reference.

TECHNICAL FIELD

This disclosure relates to ultrasonic transducers and more particularly to piezoelectric ultrasonic transducers.

DESCRIPTION OF THE RELATED TECHNOLOGY

Thin film piezoelectric micromechanical ultrasonic transducers (PMUTs) are attractive candidates for numerous applications such as biometric sensor systems (including but not limited to fingerprint sensor systems), gesture detection systems, microphones and speakers, ultrasonic imaging systems and chemical sensor systems. PMUTs typically include a piezoelectric stack suspended over a cavity. The piezoelectric stack may include a layer of piezoelectric material and a layer of patterned or unpatterned electrodes on each side of the piezoelectric layer. Although some PMUTs and PMUT-based devices can provide satisfactory results, improved PMUTs and PMUT-based devices would be desirable.

SUMMARY

The systems, methods and devices of this disclosure each have several innovative aspects, no single one of which is solely responsible for the desirable attributes disclosed herein.

At least one innovative aspect of the subject matter described in this disclosure relates to an apparatus that includes a segmented piezoelectric micromechanical ultrasonic transducer (PMUT) element. The segmented PMUT element may include a substrate, an anchor structure disposed on the substrate and a membrane disposed proximate the anchor structure. The membrane may include a piezoelectric layer stack and a mechanical layer.

In some examples, the anchor structure may include boundary portions that divide the segmented PMUT element into segments. Each segment may have a corresponding segment cavity. In some implementations, the boundary portions may correspond to nodal lines of the entire membrane. The membrane may include a membrane segment disposed proximate each segment cavity. The membrane may be configured to undergo one or both of flexural motion and vibration when the segmented PMUT element receives or transmits ultrasonic signals.

In some implementations, the boundary portions may correspond to nodal lines of first-order harmonics, second-order harmonics or higher-order harmonics of the entire membrane. In this document, the term "harmonic" is synonymous with the term "oscillation mode" or simply "mode." According to some such implementations, the membrane segments may be configured to resonate at frequencies that may correspond with the first-order modes, second-order modes or higher-order modes.

According to some examples, the segmented PMUT element may have a substantially circular shape. The boundary portions may extend along one or more diameters of the segmented PMUT element. According to some such examples, a first boundary portion may be substantially orthogonal to a second boundary portion. According to some such implementations, the segments may be substantially semicircular or quarter circular. However, in alternative implementations, the segmented PMUT element may have another shape, such as a substantially hexagonal, square or rectangular shape.

In some examples, the piezoelectric layer stack may include a piezoelectric layer, a first electrode layer disposed on a first side of the piezoelectric layer, and a second electrode layer disposed on a second side of the piezoelectric layer. For example, the piezoelectric layer stack may include a piezoelectric layer, a lower electrode layer disposed below the piezoelectric layer, and an upper electrode layer disposed above the piezoelectric layer. According to some such examples, the first electrode layer and the second electrode layer may be configured such that each segment of the segmented PMUT element may be separately controllable. In some such examples, the segmented PMUT element may be configured to provide beam steering via individual segments of the segmented PMUT element. However, in alternative implementations, the upper electrode layer and the lower electrode layer may be configured such that all segments of the segmented PMUT element may be configured to be driven in phase. For example, the control system 106 may be configured for providing electrical signals to the upper electrode layer and the lower electrode layer such that all segments of the segmented PMUT element are driven in phase.

According to some implementations, the apparatus may include an array of PMUT elements. The array of PMUT elements may include multiple instances of the segmented PMUT element. In some examples, the array may include at least one unsegmented PMUT element. The unsegmented PMUT element may include a membrane configured to resonate at a fundamental frequency that corresponds with a zeroth-order mode. According to some examples, an anchor structure of the unsegmented PMUT element may not include boundary portions for dividing the unsegmented PMUT element into segments.

In some implementations, the substrate may include a curved surface. According to some such implementations, the array of PMUT elements may be disposed on the curved surface. In some examples, at least a portion of the substrate may include flexible material. According to some examples, the apparatus may be an ultrasonic imaging device that includes the array of PMUT elements.

Other innovative aspects of the subject matter disclosed herein may be implemented in an apparatus that includes a segmented PMUT element. In some examples, the segmented PMUT element may include a substrate, an anchor structure disposed on the substrate and a membrane disposed proximate the anchor structure. The membrane may include a piezoelectric layer stack and a mechanical layer.

In some examples, the anchor structure may include boundary portions that divide the segmented PMUT element into segments. Each segment may have a corresponding segment cavity. According to some examples, the segmented PMUT element may have a substantially circular shape. The boundary portions may extend along one or more diameters of the segmented PMUT element. The membrane may include a membrane segment disposed proximate each segment cavity. The membrane may be configured to undergo one or both of flexural motion and vibration when the segmented PMUT element receives or transmits ultrasonic signals.

According to some such examples, a first boundary portion may be substantially orthogonal to a second boundary portion. According to some such implementations, the segments may be substantially semicircular or quarter circular. However, in alternative implementations, the segmented PMUT element may have another shape, such as a substantially hexagonal, square or rectangular shape.

In some implementations, the boundary portions may correspond to nodal lines of the entire membrane. In some such implementations, the boundary portions may correspond to nodal lines of first-order modes, second-order modes or higher-order modes of the entire membrane. According to some such implementations, the membrane segments may be configured to resonate at frequencies that may correspond with the first-order modes, second-order modes or higher-order modes.

In some examples, the apparatus may include an array of PMUT elements. The array may include multiple instances of the segmented PMUT element. According to some examples, the array may include at least one unsegmented PMUT element. According to some such examples, the unsegmented PMUT element may include a membrane configured to resonate at a fundamental frequency that corresponds with a zeroth-order mode.

BRIEF DESCRIPTION OF THE DRAWINGS

Details of one or more implementations of the subject matter described in this specification are set forth in this disclosure and the accompanying drawings. Other features, aspects, and advantages will become apparent from a review of the disclosure. Note that the relative dimensions of the drawings and other diagrams of this disclosure may not be drawn to scale. The sizes, thicknesses, arrangements, materials, etc., shown and described in this disclosure are made only by way of example and should not be construed as limiting. Like reference numbers and designations in the various drawings indicate like elements.

DETAILED DESCRIPTION

Figure 1A:
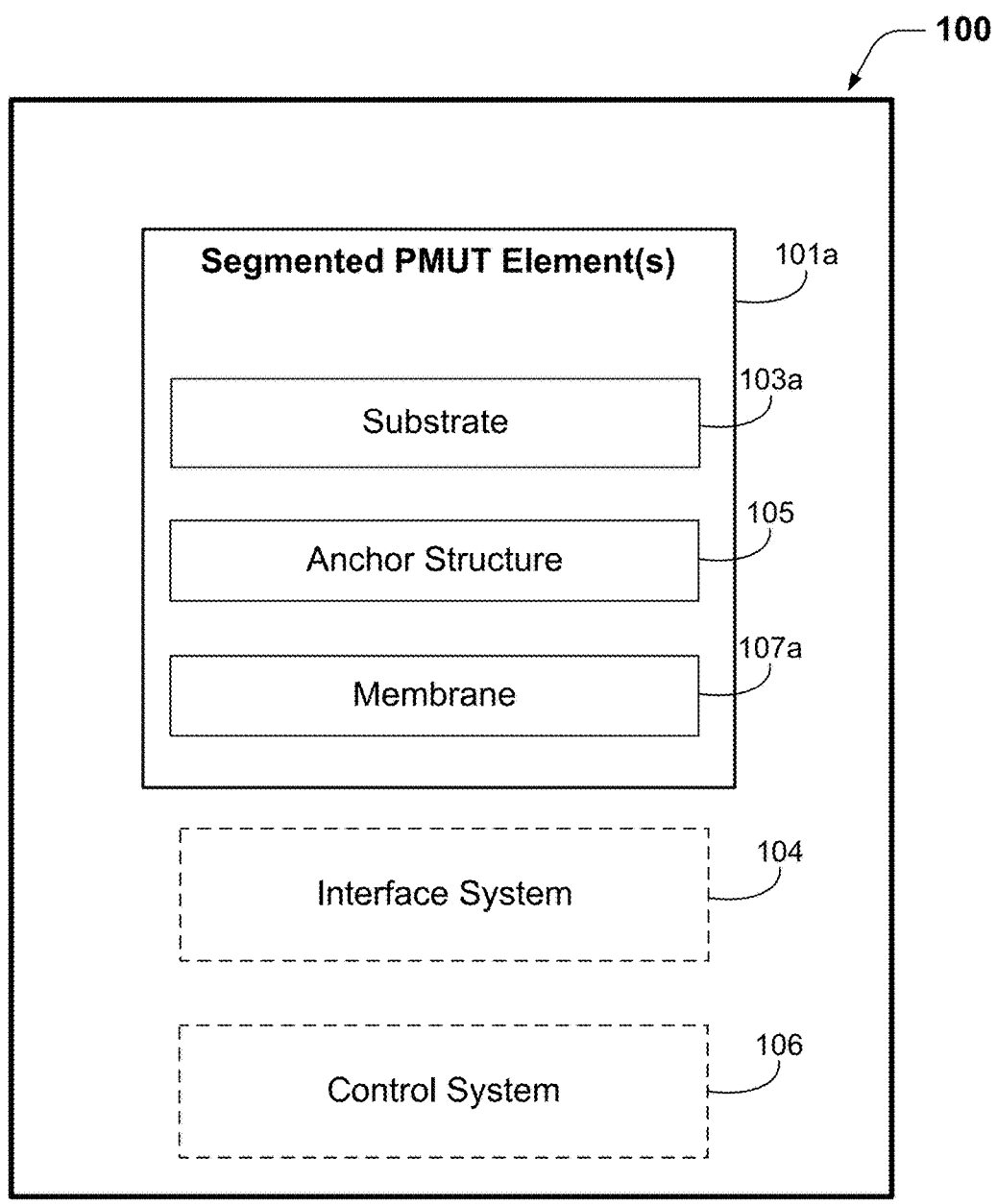
FIG. 1A is a block diagram that shows example elements of an apparatus that includes at least one PMUT element.

The following description is directed to certain implementations for the purposes of describing the innovative aspects of this disclosure. However, a person having ordinary skill in the art will readily recognize that the teachings herein may be applied in a multitude of different ways. The described implementations may be implemented in any device, apparatus, or system that includes an ultrasonic sensor. For example, it is contemplated that the described implementations may be included in or associated with a variety of electronic devices such as, but not limited to: medical devices, including but not limited to ultrasonic imaging devices, charging devices, communications devices such as mobile telephones, multimedia Internet enabled cellular telephones, mobile television receivers, wireless devices, smartphones, Bluetooth® devices, personal data assistants (PDAs), wireless electronic mail receivers, handheld or portable computers, netbooks, notebooks, smartbooks, tablets, printers, copiers, scanners, facsimile devices, global positioning system (GPS) receivers/navigators, cameras, digital media players (such as MP3 players), camcorders, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), electronic photographs, electronic billboards or signs, projectors, architectural structures, microwaves, refrigerators, stereo systems, cassette recorders or players, DVD players, CD players, VCRs, radios, portable memory chips, washers, dryers, washer/dryers, parking meters, packaging (such as in electromechanical systems (EMS) applications including microelectromechanical systems (MEMS) applications, as well as non-EMS applications), aesthetic structures (such as display of images on a piece of jewelry or clothing) and a variety of EMS devices. The teachings herein also may be used in applications such as, but not limited to, electronic switching devices, radio frequency filters, sensors, accelerometers, gyroscopes, motion-sensing devices, magnetometers, inertial components for consumer electronics, parts of consumer electronics products, varactors, liquid crystal devices, electrophoretic devices, drive schemes, manufacturing processes and electronic test equipment. Thus, the teachings are not intended to be limited to the implementations depicted solely in the Figures, but instead have wide applicability as will be readily apparent to one having ordinary skill in the art.

The systems, methods and devices of the disclosure each have several innovative aspects, no single one of which is solely responsible for the desirable attributes disclosed herein. One innovative aspect of the subject matter described in this disclosure can be implemented in a PMUT element that has a segmented membrane. (The terms "PMUT element," "PMUT" and "sensor pixel" may be used interchangeably herein.) In some implementations, the PMUT element's membrane may be segmented according to nodal lines of the entire membrane. According to some such implementations, the PMUT element's membrane may be segmented according to first-order or second-order modes of the entire membrane. Segments of the PMUT element may be configured to resonate at frequencies that correspond with the first-order or second-order modes.

In some such examples, the PMUT element's entire membrane may have a circular shape, or a substantially circular shape. According to some such examples, the PMUT element's membrane may be segmented along one or more diameters of the circular shape. Some such PMUT elements may include membranes that are segmented into semicircles, whereas other such PMUT elements may include membranes that are segmented into quarter circles. In alternative examples, the PMUT element's entire membrane may have an elliptical shape, an oval shape, a square shape, a rectangular shape, etc.

Various aspects of the subject matter described in this disclosure can be implemented in an apparatus that includes an array of PMUT elements. In some implementations, the array may include segmented PMUT elements. In some such implementations the array may include segmented PMUT elements and unsegmented PMUT elements. For example, the array may include segmented PMUT elements and unsegmented PMUT elements having the same radius or diameter. The unsegmented PMUT elements may be may be configured to resonate at a fundamental frequency that corresponds with a zeroth-order mode, whereas the segmented PMUT elements may be configured to resonate at frequencies that correspond with the first-order or second-order modes.

Implementations that include a PMUT array that has segmented PMUT elements and unsegmented PMUT elements have various potential advantages. For example, medical practitioners desire an ultrasonic imaging system that can span frequencies from 2 MHz to 20 MHz in one unit rather than switching between several transducer heads according to on the medical examination requirements. Moreover, medical practitioners desire ultrasonic imaging systems that are relatively smaller and more portable than prior art ultrasonic imaging systems. Enabling the broad frequency range in a single PMUT array would require PMUT elements having many different diameters packed into the same array (or multiple separate arrays) to fulfill this requirement, along with complicated drive electronics.

However, implementations that include a PMUT array that has segmented PMUT elements and unsegmented PMUT elements can provide multiple transmit/receive frequencies yet have the same diameter or radius, thus reducing the number of PMUT sizes needed in a single array while still spanning a desired frequency range, such as the 2-20 MHz range. In some examples, the PMUT array size may be reduced by efficient packing.

FIG. 1A is a block diagram that shows example elements of an apparatus that includes at least one PMUT element. In this example, the apparatus 100 includes at least one segmented PMUT element 101a. In some such examples, the apparatus 100 includes an array of segmented PMUT elements 101a. In some such examples, the apparatus 100 also may include one or more unsegmented PMUT elements. Some implementations may include an array of unsegmented PMUT elements. According to this example, the segmented PMUT element or elements 101a include a substrate 103a, an anchor structure 105 and a membrane 107a. In some implementations, the anchor 105 is disposed on the substrate and the membrane 107a is proximate the anchor structure 105. In some examples, the membrane 107a includes a piezoelectric layer stack and a mechanical layer.

The anchor structure 105 may include boundary portions that divide a segmented PMUT element 101a into segments. Each segment may have a corresponding segment cavity. In some implementations, the boundary portions may correspond to nodal lines of the entire membrane. The membrane may include a membrane segment disposed over each segment cavity. Various examples are disclosed herein.

The membrane may be configured to undergo one or both of flexural motion and vibration when the segmented PMUT element 101a receives or transmits signals. According to some examples, the signals may be ultrasonic signals.

In some implementations, the apparatus 100 includes a control system 106. The control system 106 is shown in a dashed outline in FIG. 1A to indicate that control system 106 may or may not be part of the apparatus 100, depending on the particular implementation. The control system 106 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof.

The control system 106 also may include (and/or be configured for communication with) one or more memory devices, such as one or more random access memory (RAM) devices, read-only memory (ROM) devices, etc. Accordingly, the apparatus 100 may have a memory system that includes one or more memory devices, though the memory system is not shown in FIG. 1A.

Some implementations of the apparatus 100 may include an interface system 104. In some examples, the interface system may include a wired or wireless interface system. In some implementations, the interface system may include a user interface system, one or more network interfaces, one or more interfaces between the control system 106 and a memory system and/or one or more interfaces between the control system 106 and one or more external device interfaces (e.g., ports or applications processors).

The interface system 104 may be configured to provide communication (which may include wired or wireless communication, such as electrical communication, radio communication, etc.) between other components of the apparatus 100. In some such examples, the interface system 104 may be configured to provide communication between the control system 106 and an array of the segmented PMUT elements 101a. Some such examples also may include an array of unsegmented PMUT elements. According to some such examples, a portion of the interface system 104 may couple at least a portion of the control system 106 to the array of the segmented PMUT elements 101a and/or the array of unsegmented PMUT elements, e.g., via electrically conducting material. According to some examples, the interface system 104 may be configured to provide communication between the apparatus 100 and other devices and/or human beings. In some such examples, the interface system 104 may include one or more user interfaces. The interface system 104 may, in some examples, include one or more network interfaces and/or one or more external device interfaces (such as one or more universal serial bus (USB) interfaces). In some implementations, the apparatus 100 may include a memory system. The interface system 104 may, in some examples, include at least one interface between the control system 106 and a memory system.

In some implementations, the control system 106 may reside in more than one device. For example, a portion of the control system 106 may reside in one device and another portion of the control system 106 may reside in another device, such as a mobile device (e.g., a smart phone). The interface system 104 also may, in some such examples, reside in more than one device.

Figure 1B:
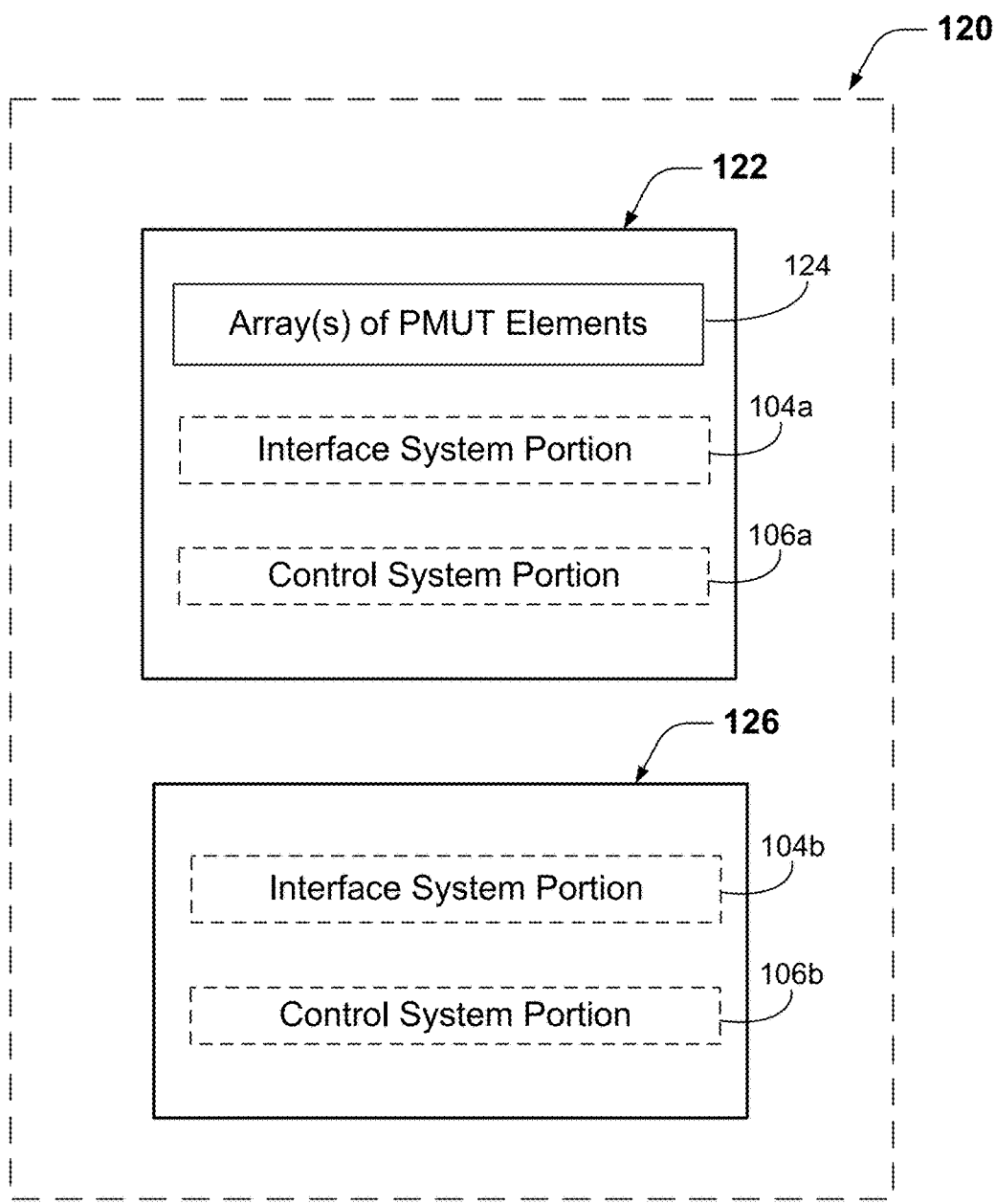
FIG. 1B is a block diagram that shows an example of a system that includes one or more arrays of PMUT elements.

FIG. 1B is a block diagram that shows an example of a system that includes one or more arrays of PMUT elements. In this example, the system 120 includes the device 122 and the device 126. According to this implementation, the device 122 includes one or more arrays of PMUT elements 124, which may include segmented PMUT elements 101*a* and/or unsegmented PMUT elements. In some examples, an array of segmented PMUT elements 101*a* and/or an array of unsegmented PMUT elements may be a one- or two-dimensional array. In some implementations, the device 122 may be a device of an ultrasonic imaging system for medical practitioners, such as a "wand" or a similar device. Here, the device 122 includes the interface system portion 104*a* and the control system portion 106*a*.

According to some examples, the device 126 may be a control module of the system 120, such as a control module of an ultrasonic imaging system. In this example, the device 126 includes the interface system portion 104*b* and the control system portion 106*b*. The interface system portions 104*a* and 104*b* may, for example, include one or more wired and/or a wireless interfaces configured to provide communication of signals between the device 122 and the device 126. The interface system portions 104*a* and 104*b* may, in some examples, include one or more user interfaces for controlling the system 120, or portions thereof.

Referring again to FIG. 1A, the control system 106 may, in some examples, be capable of controlling one or more of the segmented PMUT elements 101*a* to receive or transmit signals. According to some examples, the signals may be ultrasonic signals.

In some implementations, the control system 106 may be capable of driving all segments of a segmented PMUT element 101*a* in phase. Such implementations have the potential advantage of a simplified drive scheme, as the same drive signal may be applied to all segments of a segmented PMUT element.

However, some implementations the control system 106 may be capable of individually driving each segment of the segmented PMUT element 101*a*. Such implementations have the potential advantage of providing "in-pixel" beam steering, via individual segments of a single segmented PMUT element. According to some such implementations, the control system 106 may be configured for providing electrical signals to provide beam steering via individual segments of the segmented PMUT element.

As noted above, in some examples an array of segmented PMUT elements 101*a* and/or an array of unsegmented PMUT elements may be a one- or two-dimensional array. According to some such examples, the array of segmented PMUT elements 101*a* and/or the array of unsegmented PMUT elements may be positioned below, beside, with, on, or above a backplane of a display or an ultrasonic fingerprint sensor array.

However, in some implementations the array of PMUT elements may be disposed on a curved surface. Such implementations may be particularly advantageous for deployment in medical devices, such as wands for ultrasonic imaging applications. In some such examples, the array of PMUT elements may be disposed, at least in part, on a flexible substrate.

Figure 1C:
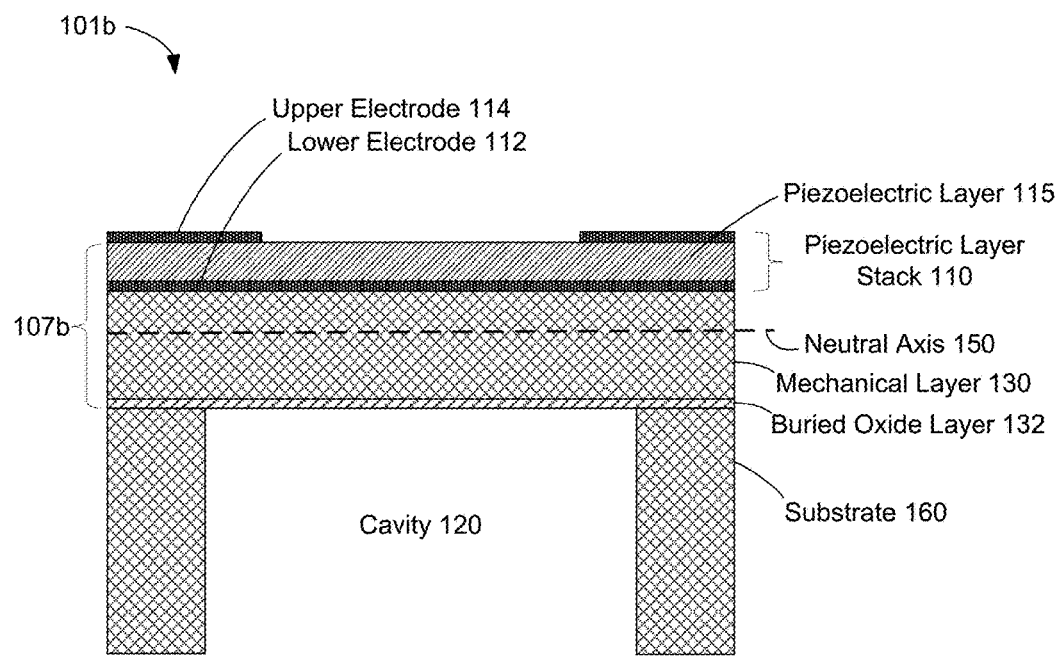
FIG. 1C shows an example of a cross-section through an unsegmented PMUT element.

FIG. 1C shows an example of a cross-section through an unsegmented PMUT element. In the example shown in FIG. 1C, unsegmented PMUT element 101*b* includes a piezoelectric layer stack 110 disposed over a mechanical layer 130 and a cavity 120 that may be formed in, for example, a silicon-on-insulator (SOI) wafer. In this implementation, the piezoelectric layer stack 110 includes a piezoelectric layer 115 with associated lower electrode 112 and upper electrode 114 disposed, respectively below and above the piezoelectric layer 115. The cavity 120 may be formed in a semiconductor substrate 160 such as a silicon wafer or in some implementations, a silicon-on-insulator (SOI) wafer. The mechanical layer 130 may, in some examples, be formed from an active silicon layer of the SOI wafer. As described in more detail below, the cavity 120 may be formed by removal of a sacrificial layer. In this example, the cavity 120 has been formed within the substrate 160, whereas in examples described below a cavity may be formed within an anchor structure that has been formed on a substrate. Accordingly, in this example, portions of the substrate 160 have a similar function to that of the anchor structures described below.

The mechanical layer 130, together with the piezoelectric layer stack 110, may form a drum-like membrane 107*b* over the cavity 120. The membrane 107*b* may be configured to undergo flexural motion and/or vibration when the unsegmented PMUT element 101*b* receives or transmits acoustic or ultrasonic signals. In the configuration illustrated in FIG. 1, the mechanical layer 130 of unsegmented PMUT element 101*b* is between the piezoelectric layer stack 110 and the cavity 120. The unsegmented PMUT element 101*b* may be capable of resonating at a fundamental frequency that corresponds with the dimensions of the cavity 120.

Various alternative implementations of PMUT elements, as well as methods for fabricating such PMUT elements, are described below. In some segmented PMUT elements described disclosed herein, the anchor structure may include boundary portions that divide a PMUT element, including the membrane, into segments. Each segment may have a corresponding segment cavity. The boundary portions may correspond to nodal lines of the entire membrane. In some such alternative implementations, the piezoelectric layer stack may be between the cavity and the mechanical layer.

In some implementations, a PMUT array may be configurable to operate in modes corresponding to multiple frequency ranges. In some implementations, for example, a control system (such as the control system 106 of FIG. 1A) may be configured for controlling the PMUT array to operate in a low-frequency mode corresponding to a low-frequency range (e.g., 50 kHz to 200 kHz) or in a high-frequency mode corresponding to a high-frequency range (e.g., 1 MHz to 25 MHz). When operating in the high-frequency mode, an apparatus may be capable of imaging at relatively higher resolution. Accordingly, in some medical ultrasonic imaging system implementations, the system may be capable of both high-resolution and lower-resolution imaging. In some display device implementations, the apparatus may be capable of detecting touch, fingerprint, stylus, and biometric information from an object such as a finger placed on the surface of the display device. In some such implementations, a high-frequency mode may correspond with a fingerprint sensor mode and a lower-frequency mode may correspond with a touch mode or a stylus mode.

When operating in a low-frequency mode, the apparatus may be capable of emitting sound waves that are capable of relatively greater penetration into air than when the apparatus is operating in the high-frequency mode. Such lower-frequency sound waves may be transmitted through various overlying layers including a cover glass, a touchscreen, a display array, a backlight, or other layers positioned between an ultrasonic transmitter and a display or sensor surface. In some implementations, a port may be opened through one or more of the overlying layers to optimize acoustic coupling from the PMUT array into air. The lower-frequency sound waves may be transmitted through the air above the display or sensor surface, reflected from one or more objects near the surface, transmitted through the air and back through the overlying layers, and detected by an ultrasonic receiver. Accordingly, when operating in the low-frequency mode, the apparatus may be capable of operating in a gesture detection mode, wherein free-space gestures near the display may be detected.

Alternatively, or additionally, in some implementations, the PMUT array may be configurable to operate in a medium-frequency mode corresponding to a frequency range between the low-frequency range and the high-frequency range (e.g., about 200 kHz to about 1 MHz). When operating in the medium-frequency mode, the apparatus may be capable of providing touch sensor functionality, although with somewhat less resolution than the high-frequency mode.

The PMUT array may be addressable for wavefront beam forming, beam steering, receive-side beam forming, and/or selective readout of returned signals. For example, individual columns, rows, sensor pixels, segments of sensor pixels and/or groups of sensor pixels may be separately addressable. A control system may control an array of transmitters to produce wavefronts of a particular shape, such as planar, circular or cylindrical wave fronts. The control system may control the magnitude and/or phase of the array of transmitters to produce constructive or destructive interference in desired locations. For example, the control system may control the magnitude and/or phase of the array of transmitters to produce constructive interference in one or more locations in which a touch or gesture has been detected.

In some implementations, PMUT devices may be co-fabricated with thin-film transistor (TFT) circuitry on the same substrate, which may be a glass or plastic substrate in some examples. The TFT substrate may include row and column addressing electronics, multiplexers, local amplification stages and control circuitry. In some implementations, an interface circuit including a driver stage and a sense stage may be used to excite a PMUT device and detect responses from the same device. In other implementations, a first PMUT device may serve as an acoustic or ultrasonic transmitter and a second PMUT device may serve as an acoustic or ultrasonic receiver. In some configurations, different PMUT devices may be capable of low- and high-frequency operation (e.g. for gestures and for fingerprint detection). In other configurations, the same PMUT device may be used for low- and high-frequency operation. In some implementations, the PMUT may be fabricated using a silicon wafer with active silicon circuits fabricated in the silicon wafer. The active silicon circuits may include electronics for the functioning of the PMUT or PMUT array.

Figure 2A:
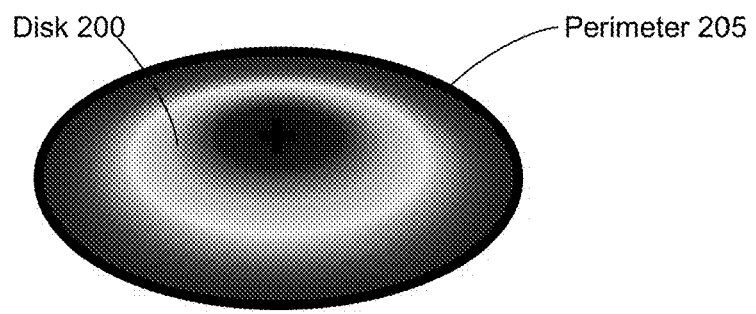
FIGS. 2A-2C show examples of modes of oscillation of a vibrating disk.
Figure 2B:
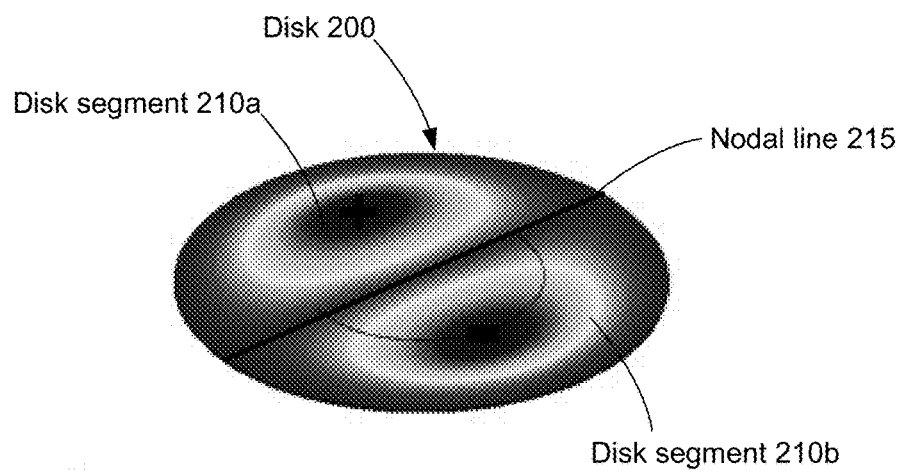
Figure 2C:
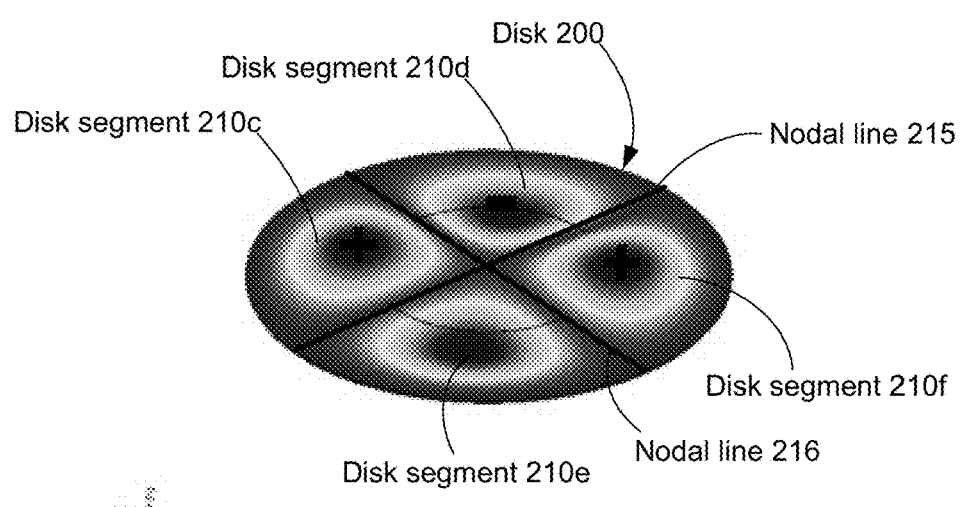

FIGS. 2A-2C show examples of modes of oscillation of a vibrating disk. The vibrating disk may, for example, correspond with a vibrating circular membrane of a PMUT element that is attached to a circular anchor structure at the perimeter of the circular membrane. In the example shown in FIG. 2A, the disk is vibrating in a fundamental or zeroth-order mode of oscillation at frequency $\omega_0$, with no internal nodal lines. In this example, the entire disk 200 is shown in a raised position relative to the perimeter 205.

In the example shown in FIG. 2B, the disk 200 is shown vibrating in a first-order mode of oscillation, at frequency $\omega_1$. In this mode of oscillation, disk segment 210a and disk segment 210b oscillate 180 degrees out of phase and are separated by a nodal line 215. In this example, the disk segment 210a is shown in a raised position and the disk segment 210b is shown in a lowered position relative to the nodal line 215. The vibrational modes of a vibrating disk are described by solutions to Bessel's equation, according to which $\omega_1 = 1.59 \omega_0$.

In the example shown in FIG. 2C, the disk 200 is shown vibrating in a second-order mode of oscillation, at frequency $\omega_2$. According to Bessel's equation, $\omega_2 = 2.13 \omega_0$. In this mode of oscillation, disk segment 210c and disk segment 210e oscillate 180 degrees out of phase and are separated by the nodal line 215. Likewise, the disk segments 210d and 210f oscillate 180 degrees out of phase and are separated by the nodal line 215. Because the disk 200 is shown vibrating in a second-order mode of oscillation, there is an additional nodal line, the nodal line 216. In this example, the disk segments 210c and 210d oscillate 180 degrees out of phase and are separated by the nodal line 216. Similarly, the disk segments 210e and 210f oscillate 180 degrees out of phase and are separated by the nodal line 216.

Based on the foregoing discussion, it may be determined that higher-order modes of oscillation for membrane segments of a PMUT element occur at fixed ratios of frequency for any radius. In other words, while the fundamental frequency $\omega_0$ is based on the dimensions (e.g., the radius) of the entire membrane, the fixed ratios of frequency corresponding to higher-order modes of oscillation for membrane segments do not depend on the radius, but are simply non-integer multiples of the fundamental frequency $\omega_0$.

Figure 3:
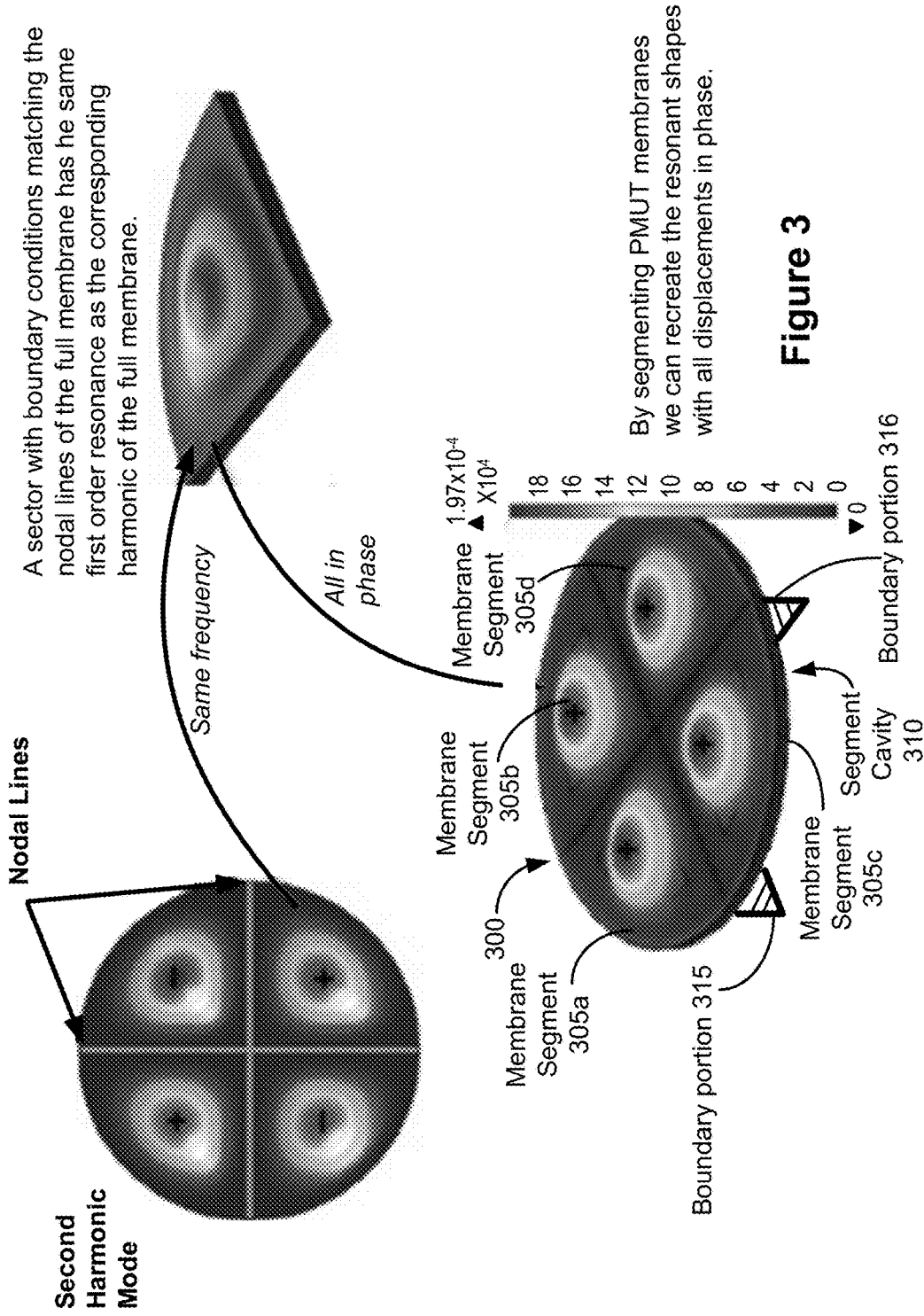
FIG. 3 shows an example of a segmented PMUT element in which an anchor structure includes boundary portions that divide the PMUT element into segments.

FIG. 3 shows an example of a segmented PMUT element in which an anchor structure includes boundary portions that divide the PMUT element into segments. In this example, the segmented PMUT element 300 includes boundary portions 315 and 316, which divide the entire membrane into membrane segments 305a, 305b, 305c and 305d. Here, each of the membrane segments 305a-305d has a corresponding segment cavity 310, which is bounded by the boundary portions 315 and 316. The anchor structure also may include a perimeter portion (not shown in FIG. 3) that supports the perimeter of the membrane segments 305a-305d. Some examples are described below with reference to FIGS. 10A-10F.

According to this implementation, the boundary portions 315 and 316 correspond to nodal lines for second-order modes of the entire membrane. Accordingly, the membrane segments 305a-305d are configured to resonate at a frequency $\omega_2$ that corresponds with the second-order modes. In this example, the segmented PMUT element 300 has a substantially circular shape and the boundary portions 315 and 316 extend along diameters of the segmented PMUT element. Accordingly, in some examples a first boundary portion (such as the boundary portion 315) may be substantially orthogonal to a second boundary portion (such as the boundary portion 316). Because the segmented PMUT element 300 has a substantially circular shape, the segments of the PMUT element and the membrane segments 305a-305d have substantially quarter circular shapes.

In some implementations, the boundary portions may correspond only to a nodal line of a first-order mode of the entire membrane, such as the nodal line 215 shown in FIG. 2B. Accordingly, the membrane segments may be configured to resonate at a frequency $\omega_1$ that corresponds with the first-order mode. Some examples are described below. If the segmented PMUT element has a substantially circular shape, the segments of the PMUT element and the membrane segments may have substantially semicircular shapes.

In the example shown in FIG. 3, all segments of the segmented PMUT element 300 are configured to be driven in phase. For example, various implementations disclosed herein have a piezoelectric layer stack that includes a piezoelectric layer, a lower electrode layer disposed below the piezoelectric layer and an upper electrode layer disposed above the piezoelectric layer. In some implementations, the upper electrode layer and the lower electrode layer may be configured such that all segments of the segmented PMUT element are configured to be driven in phase.

However, in some implementations the upper electrode layer and the lower electrode layer may be configured such that each segment of the segmented PMUT element is separately controllable. In some such implementations, the segmented PMUT element may be configured to provide beam steering via individual segments of the segmented PMUT element. For example, the upper electrode layer and the lower electrode layer may be partitioned into multiple electrode layer segments. Each of the multiple electrode layer segments may correspond to a separate segment of the segmented PMUT element.

Figure 4A:
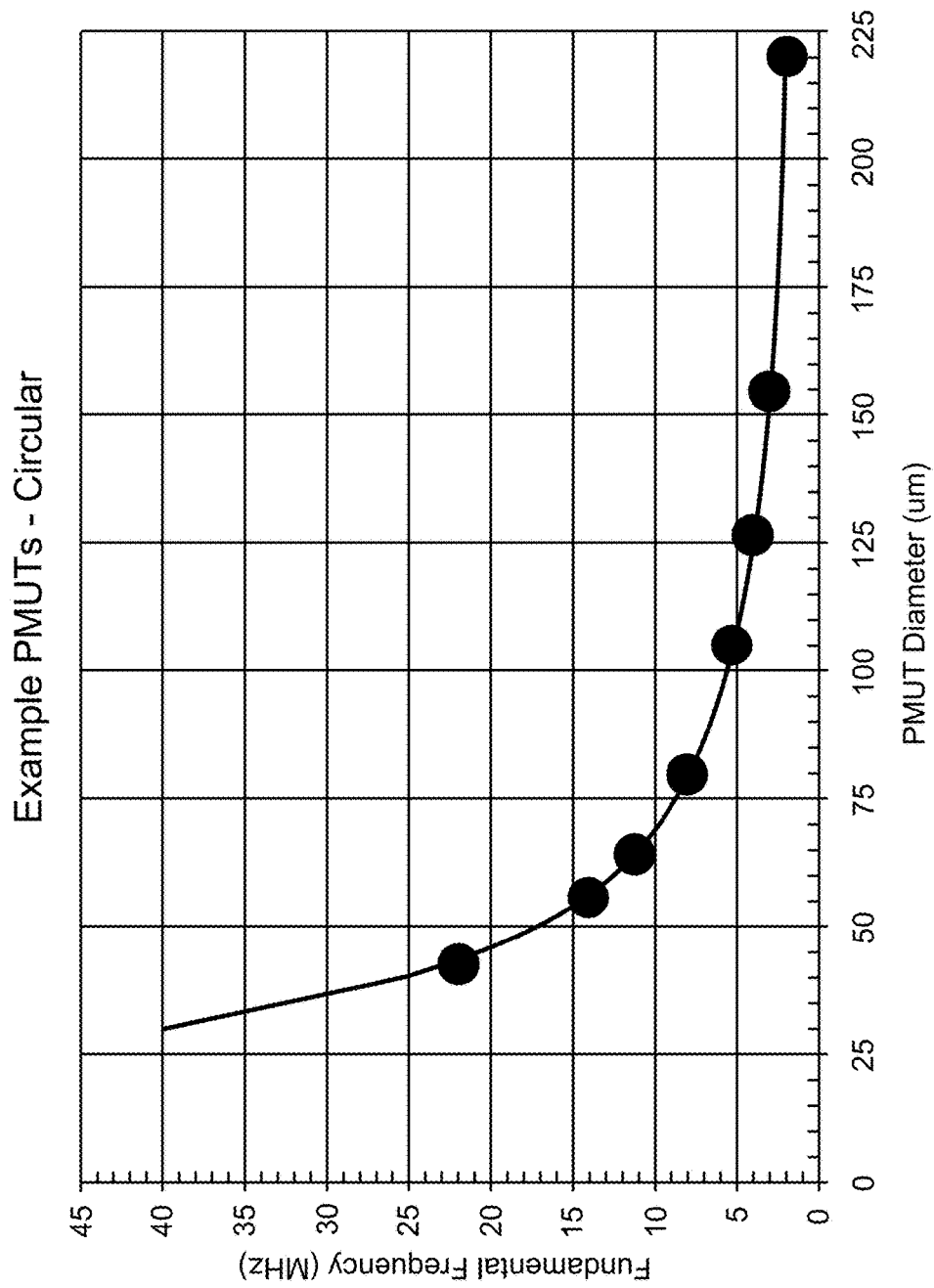
FIGS. 4A and 4B are graphs that illustrate potential advantages of some disclosed implementations.
Figure 4B:
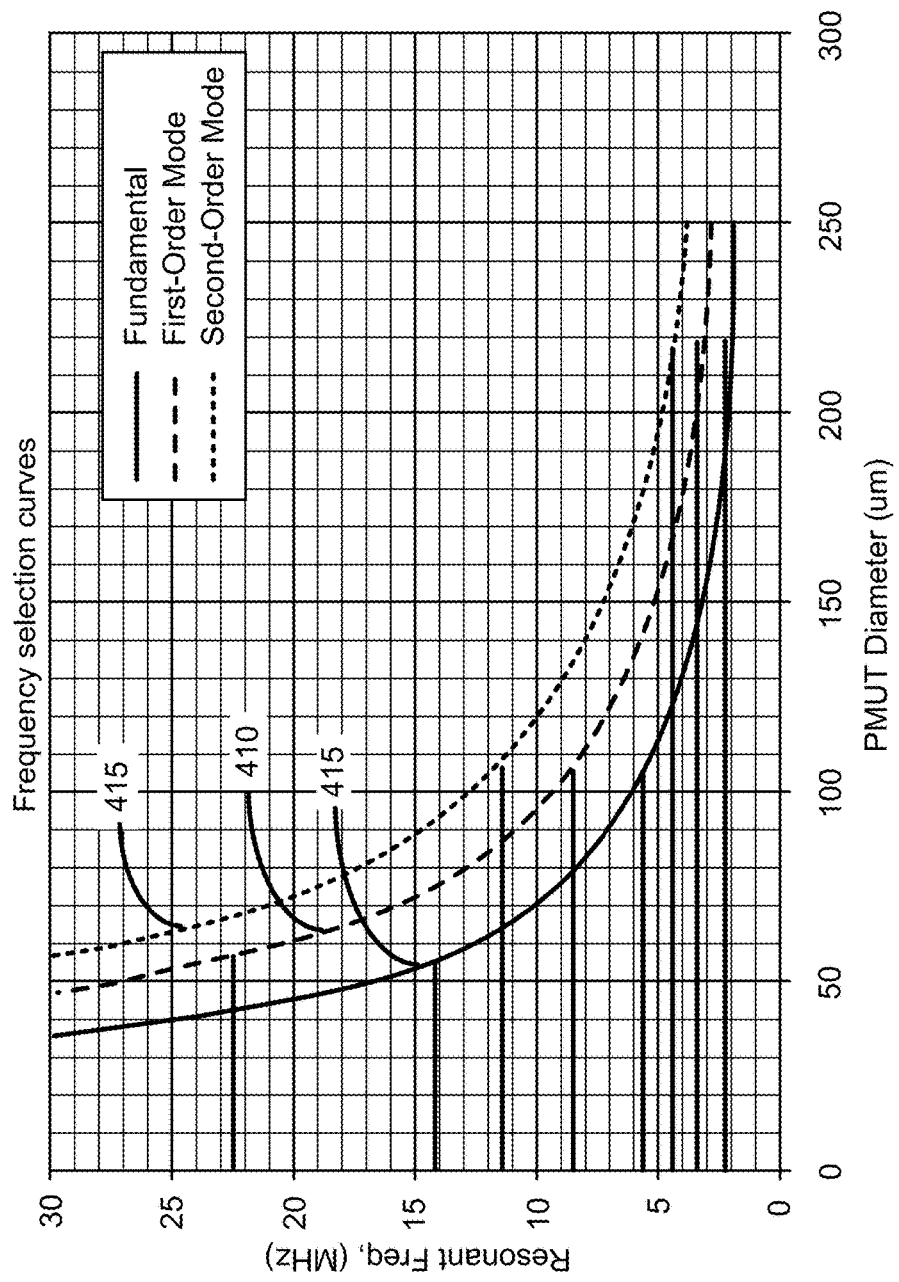

FIGS. 4A and 4B are graphs that illustrate potential advantages of some disclosed implementations. The vertical axes of FIG. 4A and FIG. 4B both indicate frequency in MHz, whereas the horizontal axes indicate the diameter of individual PMUT elements in microns. The curves 405, 410 and 415 of FIG. 4B indicate the frequencies of the fundamental, first-order mode and second-order mode corresponding to each radius.

FIG. 4A indicates that if only unsegmented, circular PMUT elements are included in a PMUT array, it would be necessary to include PMUT elements having 8 different radii in the PMUT array in order to span the required frequency range of 2-20 MHz for medical ultrasonic imaging device applications with 8 different frequency settings. In this example, the radii range in size from about 40 to 220 microns.

However, as shown in FIG. 4B, by including segmented, circular PMUT elements in a PMUT array, it would only be necessary to include PMUT elements having 3 different radii in the PMUT array in order to span the frequency range of 2-20 MHz with 8 different frequency settings.

Figure 5A:
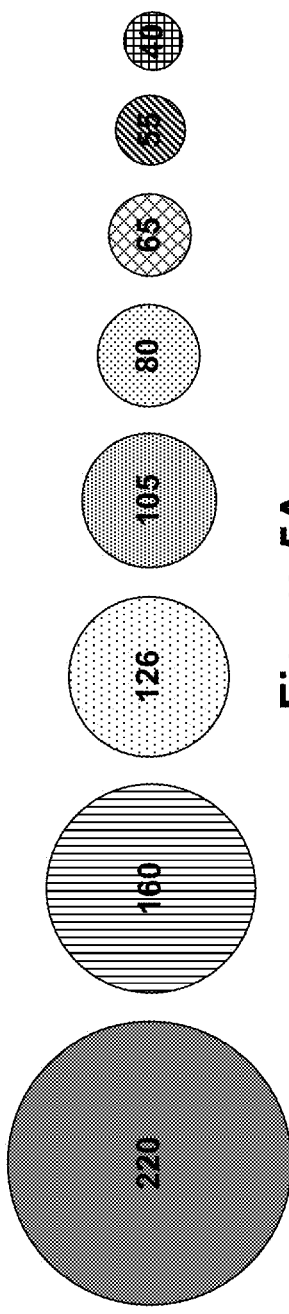
FIG. 5A indicates PMUT elements having 8 different radii, which correspond with the 8 radii indicated in FIG. 4A.
Figure 5B:
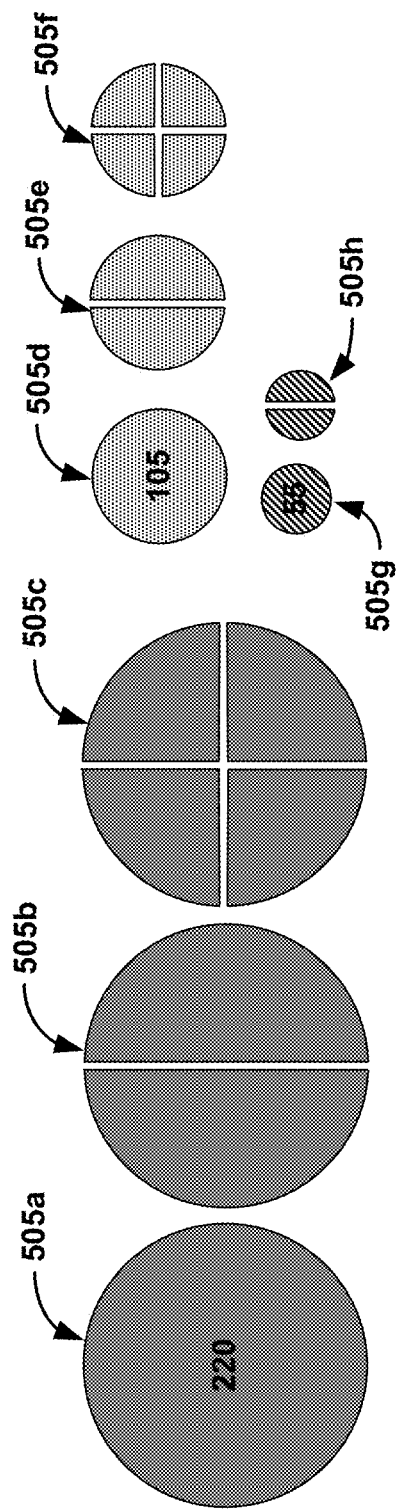
FIG. 5B indicates PMUT elements having the 3 different radii indicated in FIG. 4B.

FIG. 5A indicate PMUT elements having 8 different radii, which correspond with the 8 radii indicated in FIG. 4A. FIG. 5B indicates PMUT elements having the 3 different radii indicated in FIG. 4B. In this example, the PMUT elements shown in FIG. 5B include both unsegmented and segmented PMUT elements. For example, the PMUT elements having a 220 micron diameter include unsegmented PMUT element 505*a*, which is configured to resonate at a fundamental frequency for a 220 micron diameter membrane. The PMUT elements having a 220 micron diameter also include segmented PMUT element 505*b*, which is configured to resonate at a frequency that corresponds with the first-order mode, and segmented PMUT element 505*b*, which is configured to resonate at a frequency that corresponds with the second-order mode.

The PMUT elements having a 105 micron diameter include unsegmented PMUT element 505*d*, which is configured to resonate at a fundamental frequency. The PMUT elements having a 105 micron diameter also include segmented PMUT element 505*e*, which is configured to resonate at a frequency that corresponds with the first-order mode, and segmented PMUT element 505*f*, which is configured to resonate at a frequency that corresponds with the second-order mode. In this example, the PMUT elements having a 55 micron diameter include unsegmented PMUT element 505*g*, which is configured to resonate at a fundamental frequency. The PMUT elements having a 55 micron diameter also include segmented PMUT element 505*e*, which is configured to resonate at a frequency that corresponds with the first-order mode.

In addition to requiring fewer PMUT element radii, the packing density of a PMUT array that includes PMUT elements such as those shown in FIG. 5B can be increased, as compared to the packing density of a PMUT array that includes PMUT elements such as those shown in FIG. 5A. Therefore, such implementations include a potential advantage of reducing the overall PMUT array size.

Figure 6:
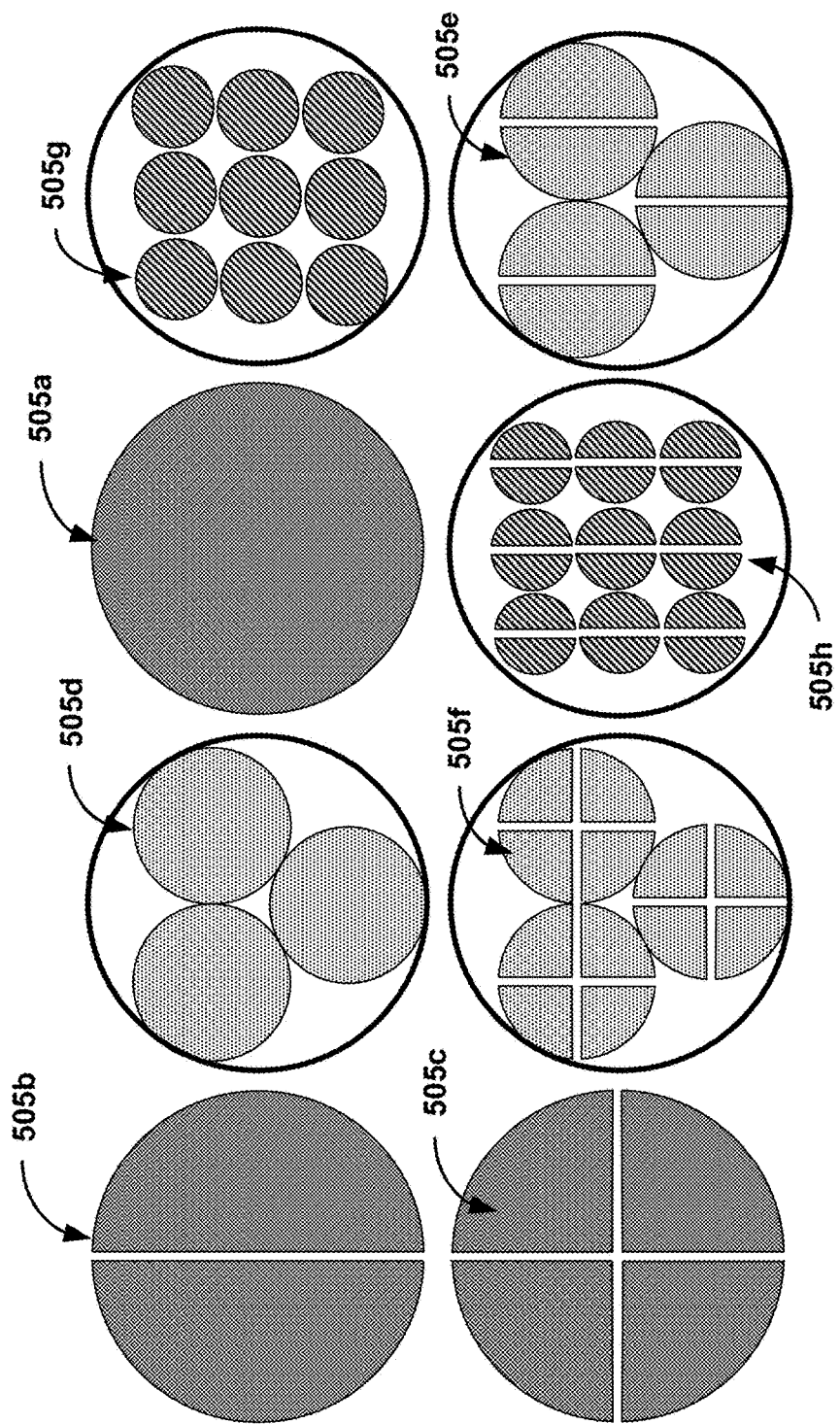
FIG. 6 shows an example of a PMUT array that includes PMUT elements such as those shown in FIG. 5B.

FIG. 6 shows an example of a PMUT array that includes PMUT elements such as those shown in FIG. 5B. In this example, the PMUT elements are arranged in a pitch that corresponds with the radius of the largest PMUT element, which is the 220 micron radius of PMUT elements 505*a*, 505*b* and 505*c*. In this implementation, three instances of the PMUT elements 505*d*, 505*e* and 505*f*, which have a 105 micron radius, can be packed into the 220 micron radius pitch. Here, nine instances of the PMUT elements 505*g* and 505*h*, which have a 55 micron radius, can be packed into the 220 micron radius pitch.

FIGS. 7A-7D show examples of implementations of a PMUT stack, configured in accordance with some aspects of the presently disclosed techniques. The examples shown in FIGS. 7A-7D may be implemented as segmented PMUT elements or unsegmented PMUT elements. For example, referring to FIG. 7A, the PMUT 700A may be formed as an unsegmented PMUT element by omitting the optional boundary portion 716. Alternatively, by including the optional boundary portion 716, the PMUT 700A may be formed as a segmented PMUT element. Only a cross-section of the optional boundary portion 716 is shown in FIGS. 7A-7D. In some implementations, the optional boundary portions 716 may have a shape like that of the boundary portion 315 or the boundary portion 316 that are shown in FIG. 3. Other implementations may include boundary portions having other shapes and/or orientations. In the illustrated implementation, a PMUT 700A includes a mechanical layer 730 disposed above a piezoelectric layer stack 710. The piezoelectric layer stack 710 includes a piezoelectric layer 715 with associated lower electrode 712 and upper electrode 714 disposed, respectively below and above the piezoelectric layer 115. In the examples shown in FIGS. 7A and 7B, a passivation layer 775 resides between the lower electrode 712 and the anchor structure 770. Mechanical layer 730 is disposed over a side of the piezoelectric stack opposite to the substrate.

The mechanical layer 730 is disposed above a side of the piezoelectric layer stack 710 opposite to a cavity 720 and, together with the piezoelectric layer stack 710, may form a drum-like membrane over the cavity 720. The membrane may be configured to undergo flexural motion and/or vibration when the PMUT receives or transmits acoustic or ultrasonic signals. In the implementation illustrated in FIG. 7A, the piezoelectric layer stack 710 is between the cavity 720 and the mechanical layer 730 whereas, in the configuration illustrated in FIG. 1, the mechanical layer 130 of PMUT 101*b* is between the piezoelectric layer stack 110 and the cavity 120. In some implementations, the mechanical layer 730 may be substantially thicker than the piezoelectric layer stack.

The mechanical layer 730 may be made of an electrically insulating material and may be deposited towards the end of the microfabrication process, i.e. after forming and patterning of the piezoelectric layer stack 710 and the cavity 720 over which the piezoelectric layer stack 710 is disposed. The mechanical layer 730 may be configured to have dimensions and mechanical properties such that a neutral axis 750 of the PMUT stack is a distance above the piezoelectric layer stack 710. More particularly, the neutral axis 750 is disposed in a plane that includes the mechanical layer 730 above the piezoelectric layer stack 710. It may be observed that the mechanical layer 730 is proximate to a side of the piezoelectric layer stack 710 that is opposite to the cavity 720 and to the substrate 760. In some implementations, the neutral axis 750 may be disposed in a plane that is substantially parallel to the piezoelectric layer stack 710, passing though the piezoelectric layer stack 710 a distance apart from the neutral axis of the piezoelectric layer stack 710 in a direction towards the mechanical layer 730.

For many multi-layer microstructural devices that include a piezoelectric layer, it is preferable for the neutral axis of the multilayer stack to be a distance apart from the neutral axis of the piezoelectric layer. For example, the mechanical layer 730 of the presently disclosed PMUT causes the neutral axis 750 of the multilayer stack to be a distance apart from the neutral axis of the piezoelectric layer 710. The distance may be determined by the thicknesses of various layers and their elastic properties, which in turn may be determined by resonant frequency and quality factor requirements for the transducer. In some implementations, the neutral axis 750 may be a distance apart from the neutral axis of the piezoelectric layer 710 and displaced towards the mechanical layer 730, yet the neutral axis 750 may still reside within the piezoelectric layer or within the piezoelectric stack. For example, the mechanical layer 730 may have a thickness to allow an out-of-plane bending mode of the multilayer stack. In some implementations, the mechanical layer 730 may be configured to allow the multilayer stack to be primarily excited in an out-of-plane mode, for example a piston mode or a fundamental mode. The out-of-plane mode can cause displacement of portions of the multilayer stack proximate to the cavity 720 (which may be referred to herein as the "released portions"), for example, at the center of a circular, square, or rectangular shaped PMUT. In some implementations, displacement of the neutral axis 750 permits transducer operation in a $d_{31}$ or $e_{31}$ mode in which the neutral axis of the multilayer stack of the membrane in the transducing area may be offset from the neutral axis of the active piezoelectric material in the stack.

As will be described in more detail below, the mechanical layer 730 may be configured to provide an encapsulation layer that seals cavity 720. In addition, the mechanical layer 730 may serve as a passivation layer for electrodes of the piezoelectric layer stack 710. By judicious selection of material properties, thickness and internal stress of the mechanical layer 730, certain transducer parameters may be improved. For example, the resonant frequency, static and dynamic deflections, acoustic pressure output, as well as membrane shape (bow) that may result from residual stresses in various layers may be tuned by appropriately configuring the mechanical layer 730.

In some implementations, the mechanical layer 730 may be configured to provide planarization for attachment of an acoustic coupling layer, for building electrical circuitry after transducer fabrication and/or to provide an insulating layer to create additional routing layers on top of the mechanical layer 730 for capacitive de-coupling with respect to the piezoelectric layer stack 710.

Figure 7A:
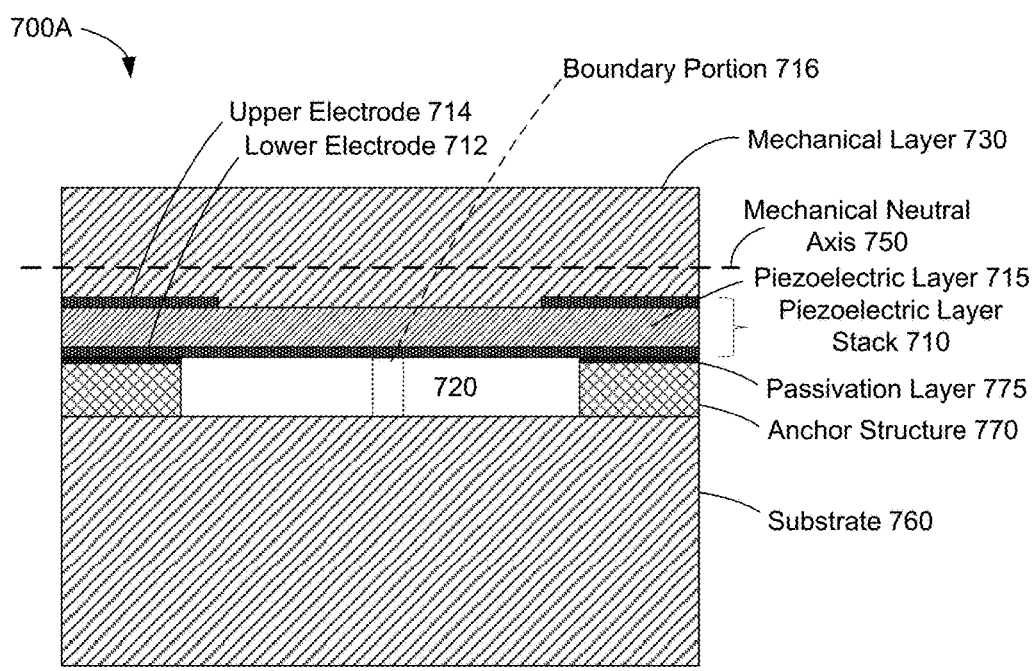
FIGS. 7A-7D show examples of implementations of a PMUT stack, configured in accordance with some aspects of the presently disclosed techniques.
Figure 7B:
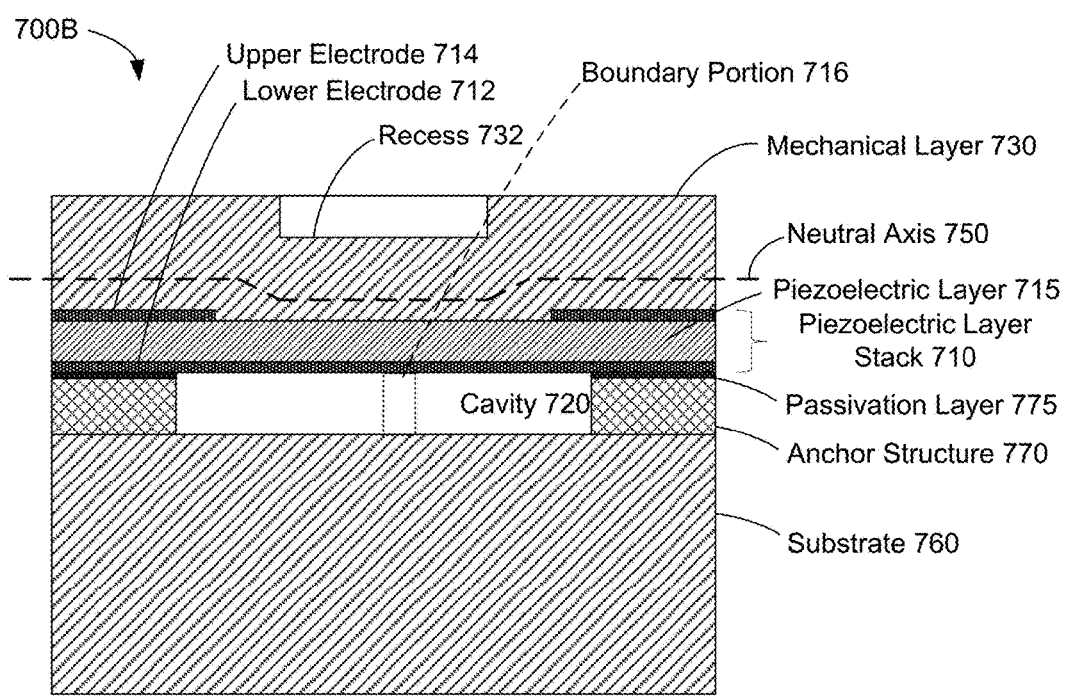

In some implementations, the mechanical layer 730 may include a recess that reduces the total thickness of part of the PMUT stack. The size and geometry of the recess and recess features may be designed to influence transducer parameters such as resonant frequency, static and dynamic deflections, acoustic pressure output, mechanical quality factor (Q), and membrane shape (bow). FIG. 7B shows a cross-sectional view of a PMUT structure having a recess 732 formed in an upper portion of the mechanical layer 730, where the mechanical layer is locally thinned. In the implementation shown, the recess 732 is formed in a central region of the mechanical layer 730 of PMUT 700B.

It may be observed that the neutral axis 750 moves downwards towards the cavity 720 proximate to the recess 732. The recess 732 may include a substantially axisymmetric feature such as a circle or a ring formed partially into a circular PMUT diaphragm near the diaphragm center, or an angular trench or portions of an angular trench formed near the periphery of a circular diaphragm. In some implementations, the recess 732 may include a square or rectangular feature formed into the mechanical layer 730 near the center of a square or rectangular PMUT diaphragm. In some implementations, recess 732 may include features such as narrow rectangles, local trenches, or slots formed near the periphery of a square, rectangular or circular diaphragm. In some implementations, a sequence of radial slots may be combined with central or peripheral recess features. In some implementations, the recess or recessed features may be formed by etching partially or substantially through the mechanical layer 730, stopping on the underlying piezoelectric layer stack 710. In some implementations, the recess 732 and/or features thereof may be formed into the mechanical layer 730 based, for example, on an etch time. In some implementations, the mechanical layer 730 may include two or more deposited layers, one of which may serve as an etch stop or barrier layer to allow precise definition of the recess and recessed features during fabrication.

Figure 7C:
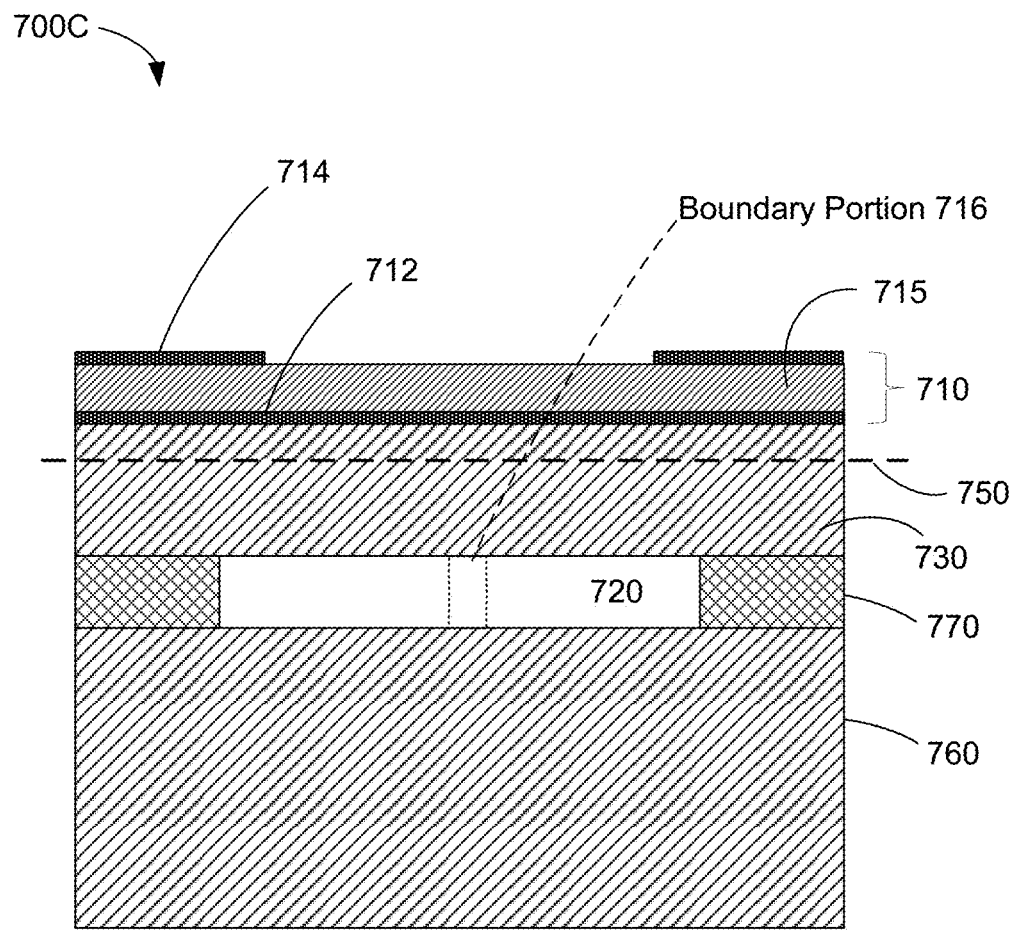

FIG. 7C shows another example of an implementation of a PMUT stack, configured in accordance with the presently disclosed techniques. In the illustrated implementation, the mechanical layer 730 of PMUT 700C is disposed above the cavity 720 and below the piezoelectric layer stack 710. Thus, the mechanical layer 730 is disposed below a side of the piezoelectric layer stack 710 that is facing the cavity 720 and the substrate 760. Together with the piezoelectric layer stack 710, the mechanical layer 730 may form a drum-like membrane or diaphragm over the cavity 720 which is configured to undergo flexural motion and/or vibration when the PMUT receives or transmits acoustic or ultrasonic signals. In some implementations, the mechanical layer 730 may be substantially thicker that the piezoelectric layer stack.

As will be described in more detail below, the mechanical layer 730 may be configured to provide an encapsulation layer that seals cavity 720. By judicious selection of material properties, thickness and internal stress of the mechanical layer 730, certain transducer parameters may be improved. For example, the resonant frequency, static and dynamic deflections, acoustic pressure output, as well as membrane shape (bow) that may result from residual stresses in various layers may be tuned by appropriately configuring the mechanical layer 730.

Figure 7D:
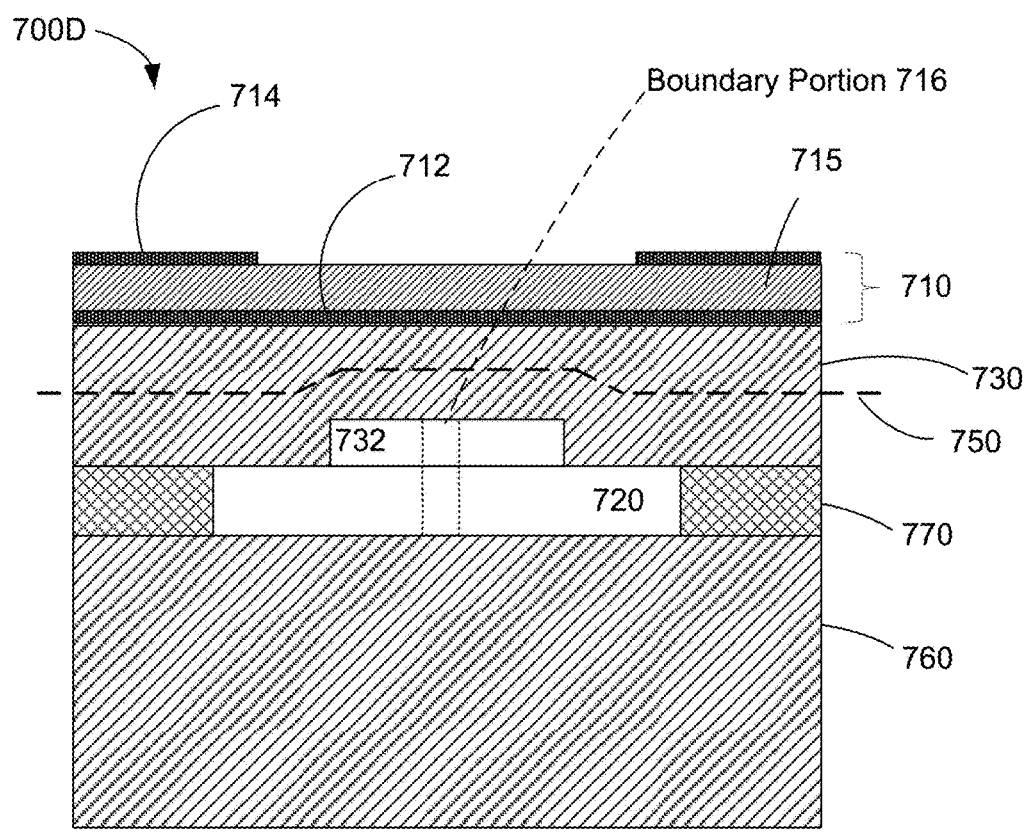

In some implementations, the mechanical layer 730 may include a recess that reduces the total thickness of part of the PMUT stack. The size and geometry of the recess and recess features may be designed to influence transducer parameters such as resonant frequency, static and dynamic deflections, acoustic pressure output, mechanical quality factor (Q), and membrane shape (bow). FIG. 7D shows a cross-sectional view of a PMUT structure having a recess 732 formed in the lower portion of the mechanical layer 730, where mechanical layer 730 is locally thinned. In the implementation shown, the recess 732 is formed in a central region of the mechanical layer 730 of PMUT 700D.

The recess 732 may include a substantially axisymmetric feature such as a circle or a ring formed partially into a circular PMUT diaphragm near the diaphragm center, or an angular trench or portions of an angular trench formed near the periphery of a circular diaphragm. In some implementations, the recess 732 may include a square or rectangular feature formed into the mechanical layer 730 near the center of a square or rectangular PMUT diaphragm. In some implementations, recess 732 may include features such as narrow rectangles, local trenches, or slots formed near the periphery of a square, rectangular or circular diaphragm. In some implementations, a sequence of radial slots may be combined with central or peripheral recess features. In some implementations, the recess or recessed features may be formed by etching partially through an underlying sacrificial layer (not shown) prior to deposition of the mechanical layer 730 and piezoelectric layer stack 710. In some implementations, the recess 732 and/or features thereof may be formed by etching partially into the underlying sacrificial layer based on an etch time. In some implementations, the sacrificial layer may include a stack of two or more deposited layers, one of which may allow local raised portions of the sacrificial layer to be formed prior to deposition of the mechanical layer 730 and piezoelectric layer stack 710, and one of which may serve as an etch stop or barrier layer to allow precise definition of the recess and recessed features during fabrication. In some implementations, the upper surface of mechanical layer 730 may be planarized prior to forming the piezoelectric layer stack 710. For example, mechanical layer 730 may be planarized with chemical-mechanical polishing (CMP), also referred to as chemical-mechanical planarization.

Figure 8:
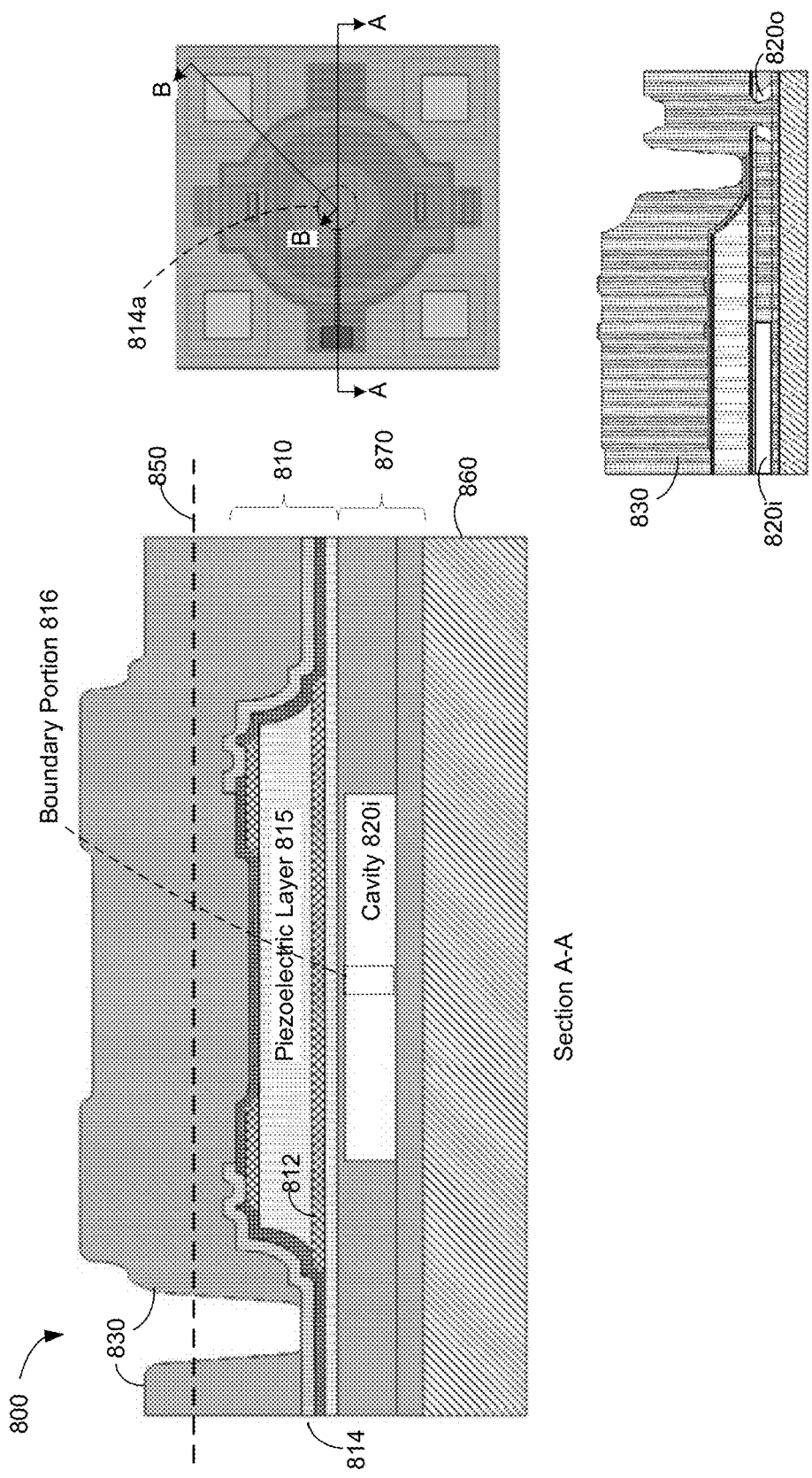
FIG. 8 illustrates another example implementation of a PMUT.

FIG. 8 illustrates another example implementation of a PMUT. The examples shown in FIGS. 8, 9A and 9B may be implemented as segmented PMUT elements or unsegmented PMUT elements. For example, referring to cross-section A-A of FIG. 8, the PMUT 800 may be formed as an unsegmented PMUT element by omitting the optional boundary portion 816. Alternatively, by including the optional boundary portion 816, the PMUT 800 may be formed as a segmented PMUT element. Only a cross-section of the optional boundary portion 816 is shown in FIG. 8. In some implementations, the optional boundary portions 816 may have a shape like that of the boundary portion 315 or the boundary portion 316 that are shown in FIG. 3. Other implementations may include boundary portions having other shapes and/or orientations. The illustrated PMUT 800 includes a piezoelectric layer stack 810 disposed above a cavity 820i. As described in more detail below, the cavity 820i may be formed by removal of a sacrificial layer formed within an anchor structure 870 through one or more release holes 820o. The anchor structure 870 may be deposited on a substrate 860, as described in more detail below. For scalability, it is preferred that these structures are made using processes common in IC, MEMS and LCD industries.

In the illustrated implementation, the piezoelectric layer stack 810 includes a piezoelectric layer 815 disposed between a lower electrode 812 and an upper electrode 814. In the top-down view of FIG. 8, an optional central portion 814a of the upper electrode 814 is shown. Some alternative implementations of the other PMUTs disclosed herein may include a central portion like the central portion 814a. A mechanical layer 830 is disposed above a side of the piezoelectric layer stack 810 opposite to a cavity 820i and, together with the piezoelectric layer stack 810, may form a drum-like membrane or diaphragm over the cavity 820i which is configured to undergo flexural motion and/or vibration when the PMUT receives or transmits acoustic or ultrasonic signals. In some implementations, the mechanical layer 830 may be configured so as to provide that the neutral axis 850 is disposed substantially external to (above) the piezoelectric layer stack 810. Advantageously, the mechanical layer 830 may serve as an encapsulation layer that seals the one or more release holes 820o and isolates the cavity 820i from external liquids and gases, as shown in Section B-B of FIG. 8, while also providing additional structural support for the PMUT 800.

Figure 9A:
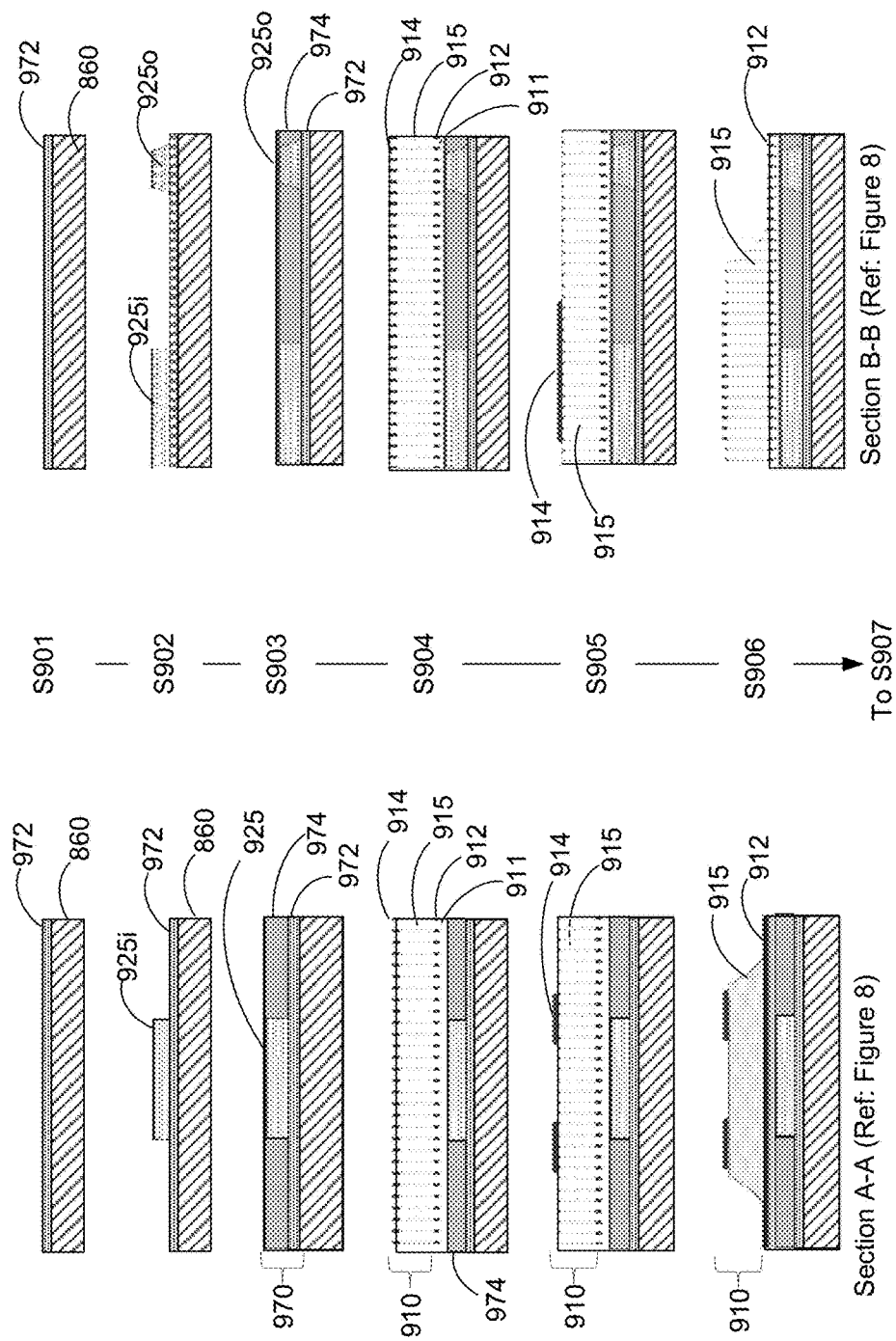
FIGS. 9A and 9B illustrate an example of a process flow for fabricating a PMUT.
Figure 9B:
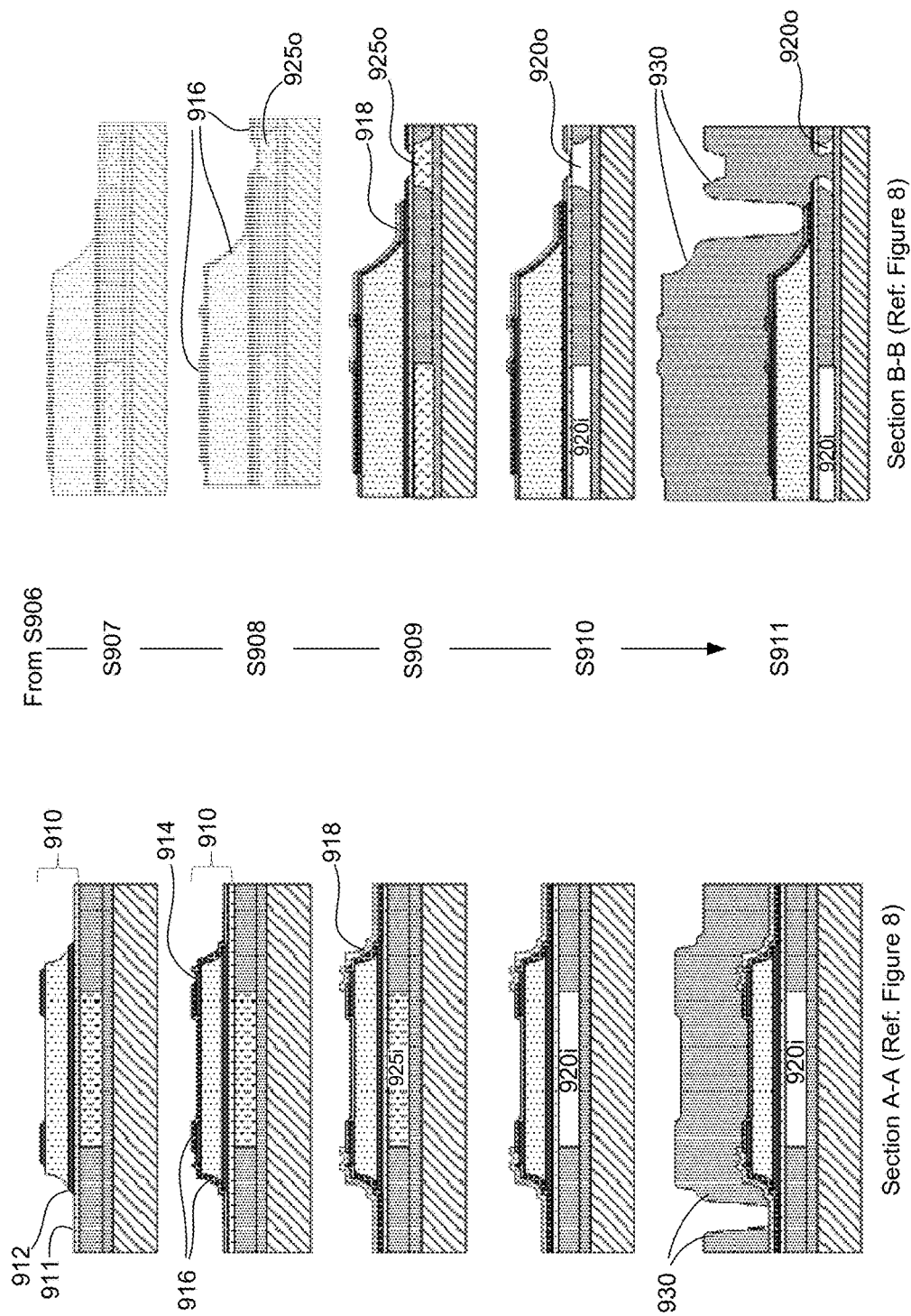

FIGS. 9A and 9B illustrate an example of a process flow for fabricating a PMUT. In the illustrated example, at step S901, a first layer portion 972 of an anchor structure 970 is deposited onto substrate 860. The first layer portion 972 may also be referred to as an oxide buffer layer. In some implementations, the oxide buffer layer 972 may be a silicon dioxide ($SiO_2$) layer having a thickness in the range of about 500 to about 30,000 Å. For example, in an implementation the thickness of the oxide buffer layer 972 is about 5,000 Å. The substrate 360 may be a glass substrate, a silicon wafer, or other suitable substrate material.

In the illustrated example, at step S902, sacrificial regions 925i and 925o may be formed by first depositing a sacrificial layer 925 of a sacrificial material that may include amorphous silicon (a-Si), polycrystalline silicon (poly-Si), or a combination of a-Si and poly-Si onto the oxide buffer layer 972. Alternatively, other sacrificial layer materials may be used such as molybdenum (Mo), tungsten (W), polyethylene carbonate (PEC), polypropylene carbonate (PPC) or polynorbornene (PNB). Step S902 may also include patterning and etching the sacrificial layer 925 to form the sacrificial regions 925i and 925o. Inner sacrificial region 925i may be disposed at a location corresponding to cavity 320i of FIG. 3, whereas outer sacrificial region 925o may be disposed at a location corresponding to the release hole 320o. One or more release channels or release vias of sacrificial layer material (not illustrated) may connect the outer sacrificial region 925o with the inner sacrificial region 925i. In some implementations using PEC, PPC or PNB, release channels or release vias may not be needed to form underlying cavities in the PMUTs, as these sacrificial materials may be thermally decomposed to produce gaseous byproducts such as carbon dioxide ($CO2$), monatomic or diatomic hydrogen, or monatomic or diatomic oxygen that may diffuse through the somewhat permeable overlying layers. In some implementations, the sacrificial layer 925 has a thickness in the range of about 500 to 20,000 Å. For example, in an implementation the thickness of the sacrificial layer 925 is about 10,000 Å.

In the illustrated example, at step S903, an anchor portion 974 of the anchor structure 970 is deposited onto the oxide buffer layer 972, so as to encompass the sacrificial regions 925i and 925o. In some implementations, the anchor portion 974 may be an $SiO_2$ layer having a thickness in the range of about 750 to about 22,000 Å. For example, in an implementation the thickness of the anchor portion 974 is about 12,000 Å. Following deposition, the anchor portion 974 may optionally undergo chemical mechanical planarization (CMP) to planarize the upper portions of the deposited layers. Alternatively, or in addition, the anchor portion 974 may be thinned with a chemical, plasma, or other material removal method.

In the illustrated example, at step S904, a piezoelectric layer stack 910 is formed on the anchor structure 970. More particularly, in some implementations a sequence of deposition processes may be carried out that results in a first layer (or "barrier layer") 911 of aluminum nitride (AlN), silicon dioxide (SiO$_2$) or other suitable etch-resistant layer being deposited onto the anchor structure 970 and sacrificial regions 925i and 925o; a lower electrode layer 912 of molybdenum (Mo), platinum (Pt) or other suitable conductive material being deposited onto the barrier layer 911; a piezoelectric layer 915 such as AlN, zinc oxide (ZnO), lead-zirconate titanate (PZT) or other suitable piezoelectric material being deposited onto the lower electrode layer 912; and an upper electrode layer 914 of Mo, Pt or other suitable conductive layer being deposited onto the piezoelectric layer 915. In some implementations, the barrier layer 911 may have a thickness in the range of about 300 to 1000 Å. For example, in an implementation the thickness of the barrier layer 911 is about 500 Å. In some implementations, the lower electrode layer 912 may have a thickness in the range of about 1000 to 30,000 Å. For example, in an implementation the thickness of the lower electrode layer 912 is about 1000 Å. In some implementations, the piezoelectric layer 915 may have a thickness in the range of about 1000 to 30,000 Å. For example, in an implementation the thickness of the active piezoelectric layer 915 is about 10,000 Å. In some implementations, the upper electrode layer 914 may have a thickness in the range of about 1000 to 30,000 Å. For example, in an implementation the thickness of the upper electrode layer 914 is about 1000 Å. The first layer or barrier layer 911 may, in some implementations, serve as a seed layer for the subsequent lower electrode and/or piezoelectric layer deposition.

Following step S904, a sequence of patterning and forming operations may be executed so as to selectively expose, in a desired geometric configuration, the various layers included in the piezoelectric layer stack 910. In the illustrated example, at step S905, the upper electrode layer 914 of molybdenum may undergo patterning and etching to expose selected areas of the piezoelectric layer 915. At step S906, the piezoelectric layer 915 of AlN or other piezoelectric material may undergo patterning and etching so as to expose selected areas of lower electrode layer 912. At step S907, the lower electrode layer 912 of molybdenum may undergo patterning and etching so as to us expose selected areas of barrier layer 911.

In the illustrated example, at step S908, an isolation layer 916 may be deposited onto the upper electrode layer 914 and other surfaces exposed during the preceding masking and etching operations of steps S904 through S907. In some implementations, the isolation layer 916 may be SiO$_2$, for example, and have a thickness in the range of about 300 to 5,000 Å. For example, in an implementation the thickness of the isolation layer 916 is about 750 Å. Step S908 may also include patterning and etching the isolation layer 916 so as to expose selected areas of upper electrode layer 914, lower electrode layer 912, and outer sacrificial region 925o. In some implementations using thermally decomposable sacrificial materials such as PEC, PPC or PNB, patterning and etching the isolation layer 916 need not expose any outer sacrificial regions 925o.

In the illustrated example, at step S909, a metal interconnect layer 918 may be deposited onto the surfaces exposed during the preceding masking and etching operations of step S908. The interconnect layer 918 may be aluminum, for example, and have a thickness in the range of about 1000 to 50,000 Å. For example, in an implementation the thickness of interconnect layer 918 is about 1000 Å. Step S909 may also include patterning and etching the interconnect layer 918 so as to expose selected areas of the isolation layer 916 and the outer sacrificial region 925o. In implementations using thermally decomposable sacrificial materials, patterning and etching the interconnect layer 918 need not expose any outer sacrificial regions 925o.

In the illustrated example, at step S910, the sacrificial material, deposited at step S902 to form inner sacrificial region 925i and outer sacrificial region 925o, may be removed, thereby forming release hole 9200 and cavity 920i. Removal of the sacrificial material from the inner sacrificial region 925i, the outer sacrificial region 925o, and one or more connecting release channels between the outer and inner sacrificial regions 925o and 925i may occur through the release hole 920o. For example, the a-Si/PolySi sacrificial layer 925 may be removed by exposing the sacrificial material to an etchant, for example xenon difluoride (XeF$_2$). By providing a release channel or via that couples outer sacrificial region 925o with inner sacrificial region 925i, substantially all of the sacrificial material of the inner sacrificial region 925i may be removed through the one or more release holes 920o. In some implementations using thermally decomposable sacrificial materials, raising the temperature of the substrate to a decomposition temperature (e.g. about 200 C for PEC and about 925 C for PNB) may selectively remove the sacrificial material, with gaseous byproducts diffusing through the overlying layers or emanating through any exposed release channels or vias during decomposition.

In the illustrated example, at step S911, a mechanical layer 930 may be deposited onto surfaces exposed during the preceding masking and etching operations of Step 909. The mechanical layer 930 may include SiO$_2$, SiON, silicon nitride (SiN), other dielectric material, or a combination of dielectric materials or layers. The mechanical layer 930 may have a thickness in the range of about 1000 to 50,000 Å. For example, in an implementation the thickness of mechanical layer 930 is about 20,000 Å. Step S909 may also include patterning and etching the mechanical layer 930 so as to achieve a desired profile. As illustrated in FIGS. 9A-9B, the mechanical layer 930 may be configured to mechanically seal (encapsulate) the release hole 920o. As a result, deposition of the mechanical layer 930 at step S911 may provide a substantial degree of isolation between the encapsulated cavity 920i and the ambient environment. The mechanical layer 930 may also serve as a passivation layer over the upper electrode layer 914 and other exposed layers. In implementations using thermally decomposable sacrificial materials, the deposition of the mechanical layer 930 may not be needed to seal or otherwise encapsulate the underlying cavity 920i.

Figure 10A:
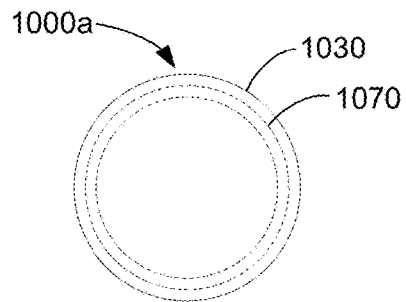
FIGS. 10A-10K show top views of various geometrical configurations of PMUTs and anchor structures.
Figure 10B:
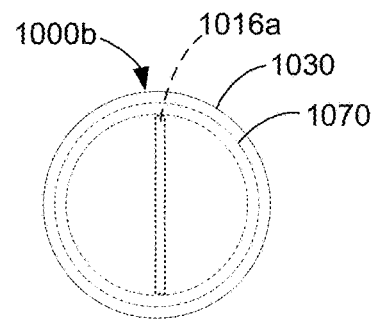
Figure 10C:
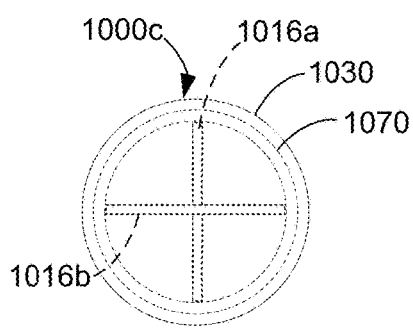

FIGS. 10A-10K show top views of various geometrical configurations of PMUTs and anchor structures. A circular unsegmented PMUT 1000a with a circular membrane 1030 and a peripheral anchor structure 1070 is shown in FIG. 10A. A circular segmented PMUT 1000b with a circular membrane 1030 and an anchor structure that includes the peripheral anchor structure 1070 and a boundary portion 1016a is shown in FIG. 10B. FIG. 10C shows a circular segmented PMUT 1000c with a circular membrane 1030 and an anchor structure that includes the peripheral anchor structure 1070 and boundary portions 1016a and 1016b.

Figure 10D:
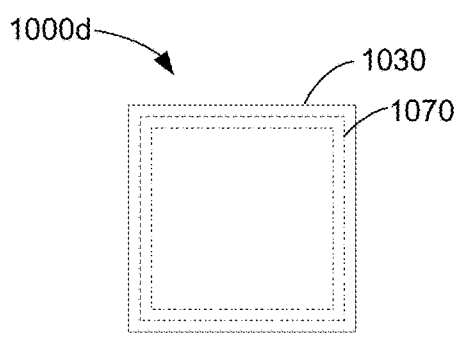
Figure 10E:
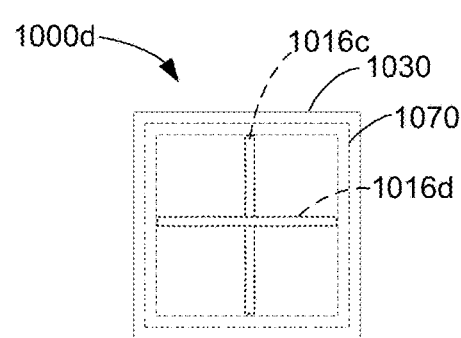

FIG. 10D shows a square unsegmented PMUT 1000d with a peripheral anchor structure 1070 and a square membrane 1030. FIG. 10E shows a segmented PMUT 1000e with an anchor structure that includes the peripheral anchor structure 1070, as well as boundary portions 1016c and 1016d. Some alternative implementations of the segmented PMUT 1000e may include only the boundary portion 1016c or the boundary portion 1016d.

Figure 10F:
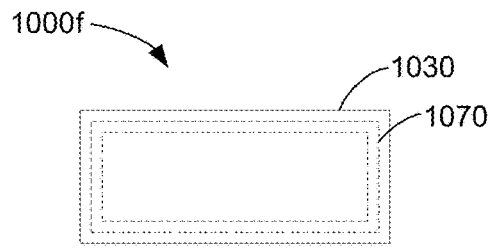
Figure 10G:
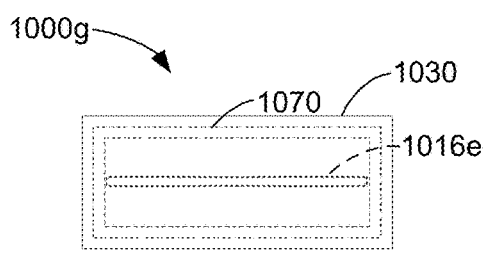

FIG. 10F shows an unsegmented long rectangular PMUT 1000f with a peripheral anchor structure 1070 and a rectangular membrane 1030. FIG. 10G shows a segmented long rectangular PMUT 1000g with an anchor structure that includes a peripheral anchor structure 1070 and a boundary portion 1016e. Some alternative implementations of the segmented PMUT 1000g may include an additional boundary portion that is perpendicular to the boundary portion 1016e.

Figure 10H:
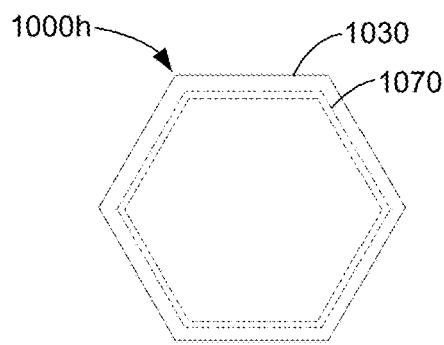
Figure 10I:
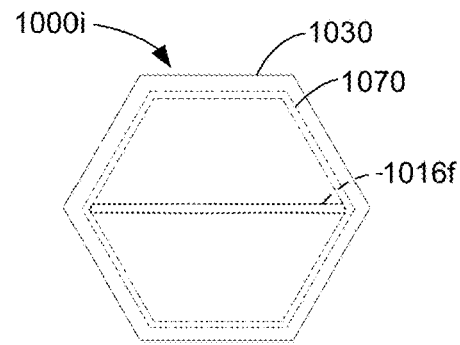
Figure 10J:
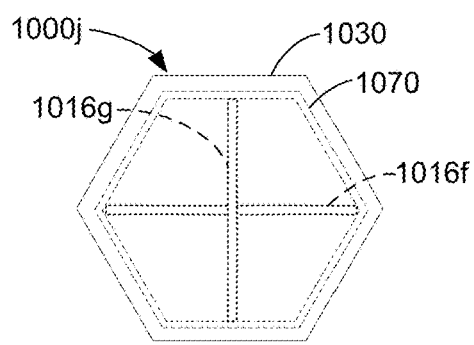
Figure 10K:
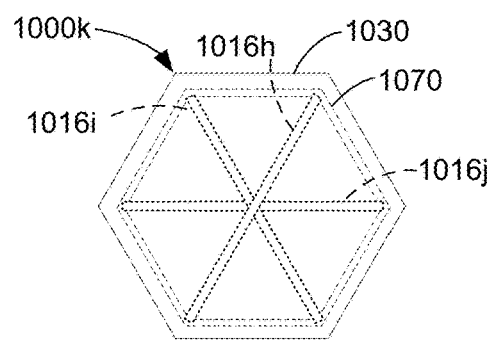

FIG. 10H shows an unsegmented hexagonal PMUT 1000h with a peripheral anchor structure 1070 and a hexagonal membrane 1030. FIG. 10I shows a segmented hexagonal PMUT 1000i with an anchor structure that includes a peripheral anchor structure 1070 and a boundary portion 1016f. FIG. 10J shows a segmented hexagonal PMUT 1000j with an anchor structure that includes a peripheral anchor structure 1070 and boundary portions 1016f and 1016g. FIG. 10K shows a segmented hexagonal PMUT 1000k with an anchor structure that includes a peripheral anchor structure 1070 and boundary portions 1016h, 1016i and 1016j. Alternative segmented hexagonal PMUTs may include a boundary portion like the boundary portion 1016g, but may not include a boundary portion like the boundary portion 1016f.

The PMUTs 1000a-1000f shown in FIGS. 10A-10K are illustrative, with connective electrodes, pads, traces, etch holes and other features omitted for clarity. In some implementations, particularly those with central or otherwise centered anchor structures, the anchor structures may be referred to as anchor posts or simply "posts". The PMUTs shown in FIGS. 10A-10K may be configured with substantial portions of the mechanical layer positioned above the piezoelectric layer stack, as shown in FIG. 7A, or with substantial portions of the mechanical layer positioned below the piezoelectric layer stack, as shown in FIG. 7C.

Thus, various types of segmented and unsegmented PMUT elements, as well as techniques for fabrication of such PMUT elements, have been disclosed. It will be appreciated that a number of alternative configurations and fabrication techniques may be contemplated.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor or any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, i.e., one or more modules of computer program instructions, encoded on a computer storage media for execution by or to control the operation of data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that can be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. Additionally, as a person having ordinary skill in the art will readily appreciate, the terms "upper" and "lower", "top" and "bottom", "front" and "back", and "over", "overlying", "on", "under" and "underlying" are sometimes used for ease of describing the figures and indicate relative positions corresponding to the orientation of the figure on a properly oriented page, and may not reflect the proper orientation of the device as implemented.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

The invention claimed is:

1. An apparatus, comprising:
a segmented piezoelectric micromechanical ultrasonic transducer (PMUT) element that includes:
a substrate;
an anchor structure disposed on the substrate;
a membrane disposed proximate the anchor structure, the membrane including a piezoelectric layer stack and a mechanical layer, wherein:
the anchor structure includes boundary portions that divide the segmented PMUT element into segments, each segment having a corresponding segment cavity;
the membrane including a membrane segment disposed proximate each segment cavity; and
the membrane is configured to undergo one or both of flexural motion and vibration when the segmented PMUT element receives or transmits ultrasonic signals.

2. The apparatus of claim 1, wherein the boundary portions correspond to nodal lines of the membrane.

3. The apparatus of claim 1, wherein the boundary portions correspond to nodal lines of first-order modes, second-order modes or higher-order modes of the membrane.

4. The apparatus of claim 3, wherein the membrane segments are configured to resonate at frequencies that correspond with the first-order modes, second-order modes or higher-order modes.

5. The apparatus of claim 1, wherein the segmented PMUT element has a substantially circular shape and wherein the boundary portions extend along one or more diameters of the segmented PMUT element.

6. The apparatus of claim 5, wherein a first boundary portion is substantially orthogonal to a second boundary portion.

7. The apparatus of claim 1, wherein the segments are substantially semicircular or quarter circular.

8. The apparatus of claim 1, wherein the piezoelectric layer stack includes a piezoelectric layer, a first electrode layer disposed on a first side of the piezoelectric layer, and a second electrode layer disposed on a second side the piezoelectric layer.

9. The apparatus of claim 8, wherein the first electrode layer and the second electrode layer are configured such that each segment of the segmented PMUT element is separately controllable.

10. The apparatus of claim 9, further comprising a control system configured for providing electrical signals to provide beam steering via individual segments of the segmented PMUT element.

11. The apparatus of claim 8, further comprising a control system configured for providing electrical signals to the first electrode layer and the second electrode layer such that all segments of the segmented PMUT element are driven in phase.

12. The apparatus of claim 1, wherein the segmented PMUT element has a substantially hexagonal, square or rectangular shape.

13. The apparatus of claim 1, further comprising an array of PMUT elements that includes multiple instances of the segmented PMUT element.

14. The apparatus of claim 13, wherein the array includes at least one unsegmented PMUT element, the unsegmented PMUT element including a membrane configured to resonate at a fundamental frequency that corresponds with a zeroth-order mode.

15. The apparatus of claim 14, wherein an anchor structure of the unsegmented PMUT element does not include boundary portions for dividing the unsegmented PMUT element into segments.

16. The apparatus of claim 13, wherein the substrate includes a curved surface and wherein the array of PMUT elements is disposed on the curved surface.

17. The apparatus of claim 13, wherein at least a portion of the substrate includes flexible material.

18. The apparatus of claim 13, wherein the apparatus comprises an ultrasonic imaging device that includes the array of PMUT elements.

19. An apparatus, comprising:
a segmented piezoelectric micromechanical ultrasonic transducer (PMUT) element that includes:
a substrate;
an anchor structure disposed on the substrate;
a membrane disposed proximate the anchor structure, the membrane including a piezoelectric layer stack and a mechanical layer, wherein:
the anchor structure includes boundary portions that divide the segmented PMUT element into segments, each segment having a corresponding segment cavity, wherein the segmented PMUT element has a substantially circular shape and wherein the boundary portions extend along one or more diameters of the segmented PMUT element;
the membrane including a membrane segment disposed proximate each segment cavity; and
the membrane is configured to undergo one or both of flexural motion and vibration when the segmented PMUT element receives or transmits ultrasonic signals.

20. The apparatus of claim 19, wherein a first boundary portion is substantially orthogonal to a second boundary portion.

21. The apparatus of claim 19, wherein the segments are substantially semicircular or quarter circular.

22. The apparatus of claim 19, wherein the boundary portions correspond to nodal lines of first-order modes, second-order modes or higher-order modes of the membrane.

23. The apparatus of claim 19, wherein the membrane segments are configured to resonate at frequencies that correspond with the first-order modes, second-order modes or higher-order modes.

24. The apparatus of claim 19, further comprising an array of PMUT elements that includes multiple instances of the segmented PMUT element.

25. The apparatus of claim 24, wherein the array includes at least one unsegmented PMUT element, the unsegmented PMUT element including a membrane configured to resonate at a fundamental frequency that corresponds with a zeroth-order mode.

* * * * *